(12) United States Patent
Dougakiuchi et al.

(10) Patent No.: US 10,591,413 B2
(45) Date of Patent: Mar. 17, 2020

(54) FLUID ANALYZER

(71) Applicant: HAMAMATSU PHOTONICS K.K., Hamamatsu-shi, Shizuoka (JP)

(72) Inventors: Tatsuo Dougakiuchi, Hamamatsu (JP); Akio Ito, Hamamatsu (JP); Kazuue Fujita, Hamamatsu (JP); Tadataka Edamura, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 16/021,055

(22) Filed: Jun. 28, 2018

(65) Prior Publication Data
US 2019/0011361 A1   Jan. 10, 2019

(30) Foreign Application Priority Data

Jul. 5, 2017 (JP) .................. 2017-131957

(51) Int. Cl.
*G01J 3/30* (2006.01)
*G01N 21/39* (2006.01)
*H01S 5/343* (2006.01)
*H01S 5/10* (2006.01)
*H01S 5/20* (2006.01)
(Continued)

(52) U.S. Cl.
CPC ..... *G01N 21/39* (2013.01); *H01L 31/035236* (2013.01); *H01S 5/0028* (2013.01); *H01S 5/0264* (2013.01); *H01S 5/10* (2013.01); *H01S 5/2027* (2013.01); *H01S 5/34313* (2013.01); *G01N 2021/391* (2013.01); *G01N 2021/451* (2013.01); *H01S 5/0203* (2013.01); *H01S 5/0208* (2013.01); *H01S 5/0656* (2013.01); *H01S 5/12* (2013.01); *H01S 5/141* (2013.01);
(Continued)

(58) Field of Classification Search
CPC ......... G01N 21/39; H01S 5/0203; H01S 5/10; H01S 5/2027; H01S 5/22; H01S 5/3401; H01S 5/34313
USPC .................................................. 356/311–318
See application file for complete search history.

(56) References Cited

U.S. PATENT DOCUMENTS

| 5,303,036 A * | 4/1994 | McLachlan ........ G01N 21/8507 356/436 |
| 7,424,044 B2 * | 9/2008 | Zheng ................... H01S 5/4062 372/50.12 |

(Continued)

OTHER PUBLICATIONS

Paul Dean et al., "Terahertz imaging through self-mixing in a quantum cascade laser," Optics Letters, Optical Society of America, Jul. 1, 2011, pp. 2587-2589, vol. 36, No. 13.

*Primary Examiner* — Sunghee Y Gray
(74) *Attorney, Agent, or Firm* — Drinker Biddle & Reath LLP

(57) ABSTRACT

A fluid analyzer includes a substrate, a quantum cascade laser formed on a surface of the substrate and including a first light-emitting surface and a second light-emitting surface facing each other in a predetermined direction parallel to the surface, a quantum cascade detector formed on the surface and including the same layer structure as the quantum cascade laser and a light incident surface facing the second light-emitting surface in the predetermined direction, and an optical element disposed on an optical path of light emitted from the first light-emitting surface across an inspection region in which a fluid to be analyzed is to be disposed and reflecting the light to feed the light back to the first light-emitting surface.

16 Claims, 11 Drawing Sheets

(51) Int. Cl.
  *H01S 5/026*    (2006.01)
  *H01S 5/00*     (2006.01)
  *H01L 31/0352*  (2006.01)
  *H01S 5/34*     (2006.01)
  *H01S 5/22*     (2006.01)
  *H01S 5/02*     (2006.01)
  *G01N 21/45*    (2006.01)
  *H01S 5/14*     (2006.01)
  *H01S 5/12*     (2006.01)
  *H01S 5/065*    (2006.01)

(52) U.S. Cl.
  CPC ............... *H01S 5/143* (2013.01); *H01S 5/22* (2013.01); *H01S 5/3401* (2013.01)

(56) References Cited

U.S. PATENT DOCUMENTS

| | | | |
|---|---|---|---|
| 2010/0029026 A1* | 2/2010 | Berger | B82Y 20/00 |
| | | | 438/24 |
| 2017/0030823 A1* | 2/2017 | Wagner | G01N 21/39 |
| 2017/0115213 A1* | 4/2017 | Ito | G01N 21/39 |
| 2017/0243994 A1* | 8/2017 | Dougakiuchi | G01N 21/3504 |

* cited by examiner

FLUID ANALYZER

TECHNICAL FIELD

The present disclosure relates to a fluid analyzer.

BACKGROUND

An imaging device that irradiates an object with light emitted from a quantum cascade laser, feeds light reflected from the object back to the quantum cascade laser, and measures a change in the electrical characteristics of the quantum cascade laser to acquire the imaging information of the object is known (see Paul Dean, et al., "Terahertz imaging through self-mixing in a quantum cascade laser", OPTICS LETTERS, Optical Society of America, Jul. 1, 2011, Vol. 36, No. 13, p. 2587-2589).

SUMMARY

The quantum cascade laser is known as one of light sources suitable for the analysis of a fluid. For example, differential optical absorption spectroscopy of light, which is emitted from the quantum cascade laser, is performed for a fluid to be analyzed to analyze the fluid. For this reason, it is important to measure the absorption or scattering of the light, which is caused by the fluid to be analyzed, with high sensitivity and high accuracy. Here, the application of a method using the above-mentioned device in the related art to the analysis of a fluid is also considered. However, since there is a case in which the influence of external factors (for example, the variations of external environments, such as the temperature and electrical noises of the quantum cascade laser) on a change in the electrical characteristics of the quantum cascade laser cannot be ignored, there is a concern that the sensitivity and accuracy of analysis may deteriorate.

An object of an aspect of the disclosure is to provide a fluid analyzer that can analyze a fluid to be analyzed with high sensitivity and high accuracy.

A fluid analyzer according to an aspect of the disclosure includes a substrate, a quantum cascade laser formed on a surface of the substrate and including a first light-emitting surface and a second light-emitting surface facing each other in a predetermined direction parallel to the surface, a quantum cascade detector formed on the surface and including the same layer structure as the quantum cascade laser and a light incident surface facing the second light-emitting surface in the predetermined direction, and an optical element disposed on an optical path of light emitted from the first light-emitting surface across an inspection region in which a fluid to be analyzed is to be disposed and reflecting the light to feed the light back to the first light-emitting surface.

In the fluid analyzer according to the aspect of the disclosure, light emitted from the first light-emitting surface is reflected by the optical element and the reflected light is fed back to the first light-emitting surface. When the light is fed back to the first light-emitting surface, light having an intensity corresponding to the intensity of the light, which is fed back to the first light-emitting surface, is emitted from the second light-emitting surface. Since the absorption or scattering of the light caused by the fluid occurs in a case in which the fluid to be analyzed is disposed in the inspection region, the intensity of the light emitted from the second light-emitting surface is changed in comparison with the intensity of the light emitted from the second light-emitting surface in a case in which the fluid is not disposed in the inspection region. Here, the light emitted from the second light-emitting surface is a laser beam that is oscillated from the second light-emitting surface as an end face of an optical resonator and has an intensity corresponding to the intensity of the light fed back to the first light-emitting surface. For this reason, a change in the intensity of the light emitted from the second light-emitting surface is likely to become more significant than a change in the electrical characteristics of the quantum cascade laser in response to the intensity of the light fed back to the first light-emitting surface. Accordingly, it is possible to measure a change in the intensity of the light fed back to the first light-emitting surface, while inhibiting sensitivity and accuracy from depending on the influence of external factors, by measuring a change in the intensity of the light emitted from the second light-emitting surface by the quantum cascade detector. Therefore, according to the fluid analyzer of the aspect of the disclosure, the fluid to be analyzed can be analyzed with high sensitivity and high accuracy.

In the fluid analyzer according to the aspect of the disclosure, an optical resonator may be forming between the first light-emitting surface and the second light-emitting surface. According to the fluid analyzer of the aspect of the disclosure, the quantum cascade laser functions as an optical resonator oscillating laser. For this reason, it is possible to perform the analysis (so-called monitoring) of the presence of the fluid in the inspection region with high sensitivity and high accuracy by setting the oscillation wavelength of the quantum cascade laser in response to the kind of the fluid to be analyzed.

In the fluid analyzer according to the aspect of the disclosure, the quantum cascade laser may be formed as a Fabry-Perot element oscillating in a multi-mode. According to the fluid analyzer of the aspect of the disclosure, since light, which is broader than light obtained in a single mode, is emitted from the first light-emitting surface of the quantum cascade laser, various fluids can be analyzed as an object to be analyzed. Further, since the oscillation of the quantum cascade laser and the detection of the light performed by the quantum cascade detector are hard to be affected by a position at which the optical element is disposed. For this reason, the degree of freedom of the layout of the optical element is improved and the quantum cascade laser and the optical element are easily aligned with each other.

In the fluid analyzer according to the aspect of the disclosure, the quantum cascade laser is formed as a distributed feedback element oscillating in a single mode, and a length of the optical path of the light up to the optical element from the first light-emitting surface may be an integer multiple of a half of an oscillation wavelength of the quantum cascade laser. According to the fluid analyzer of the aspect of the disclosure, when the oscillation wavelength of the quantum cascade laser is set to be equal to the wavelength of light absorbed or scattered by the fluid in a case in which, for example, the kind of the fluid to be analyzed is specified in advance, the intensity of the light fed back to the first light-emitting surface can be significantly changed in a case in which the fluid is disposed in the inspection region. Accordingly, the intensity of the light emitted from the second light-emitting surface can be more significantly changed. Further, since the length of the optical path of the light up to the optical element from the first light-emitting surface is the integer multiple of a half of the oscillation wavelength, light, which is fed back to the first light-emitting surface and is incident on the quantum cascade laser, and light present in the quantum cascade laser interfere with each other. Since the oscillation characteristics of the optical resonator are significantly affected with this interference, a change in the intensity of the light emitted from the second light-emitting surface becomes significant. Accordingly, the analysis of the fluid can be performed with higher sensitivity.

In the fluid analyzer according to the aspect of the disclosure, the optical element may be a diffraction grating diffracting and reflecting the light emitted from the first light-emitting surface, the diffraction grating may be driven to reflect, from among the light, light having a wavelength corresponding to an incident angle of the light, and to feed the light having the wavelength back to the first light-emitting surface, and an optical resonator may be formed between the second light-emitting surface and the diffraction grating. According to the fluid analyzer of the aspect of the disclosure, an optical resonator is formed between the second light-emitting surface and the diffraction grating. The optical resonator oscillates in a single mode with a wavelength, which corresponds to the incident angle of the light emitted from the first light-emitting surface and incident on the diffraction grating, as an oscillation wavelength. Accordingly, it is possible to perform the analysis (so-called sensing) of the composition of the fluid to be analyzed, which is disposed in the inspection region, with high sensitivity and high accuracy while actively changing the oscillation wavelength in a state in which single-mode oscillation is maintained by changing the incident angle on the diffraction grating. Further, in the fluid analyzer according to the aspect of the disclosure, an external resonator-type optical resonator in which light reciprocates between the second light-emitting surface and the diffraction grating is formed, and the inspection region is present in the optical resonator. For this reason, the light repeatedly reciprocates between the second light-emitting surface and the diffraction grating while the light is absorbed or scattered by the fluid to be analyzed. Accordingly, since the oscillation characteristics of the optical resonator are directly affected with a change in the intensity of the light present in the optical resonator, a change in the intensity of the light emitted from the second light-emitting surface becomes significant in comparison with a change in the intensity of the light emitted from the second light-emitting surface in a case in which the inspection region is present outside the optical resonator. As a result, the analysis of the fluid can be performed with higher sensitivity.

The fluid analyzer according to the aspect of the disclosure may further include a diffraction grating diffracting and reflecting the light emitted from the first light-emitting surface, and a mirror reflecting the light diffracted and reflected by the diffraction grating. The mirror may be driven to reflect, from among the light, light having a wavelength corresponding to an incident angle of the light, and to feed the light having the wavelength back to the first light-emitting surface through the diffraction grating; an optical resonator may be formed between the second light-emitting surface and the mirror; and the optical element may be disposed on an optical path of zero-order reflected light of the light reflected by the diffraction grating across the inspection region in which the fluid to be analyzed is to be disposed, and may reflect the zero-order reflected light to feed the light back to the first light-emitting surface through the diffraction grating. According to the fluid analyzer of the aspect of the disclosure, an optical resonator is formed between the second light-emitting surface and the mirror. The optical resonator oscillates in a single mode with a wavelength, which corresponds to the incident angle of the light diffracted and reflected by the diffraction grating and incident on the mirror, as an oscillation wavelength. Accordingly, it is possible to perform the analysis (so-called sensing) of the composition of the fluid to be analyzed, which is disposed in the inspection region, with high sensitivity and high accuracy while actively changing the oscillation wavelength in a state in which single-mode oscillation is maintained by changing the incident angle on the mirror.

In the fluid analyzer according to the aspect of the disclosure, the light incident surface may be inclined so as to have a positional relationship where an acute angle is formed between the light incident surface and the second light-emitting surface. According to the fluid analyzer of the aspect of the disclosure, the light emitted from the second light-emitting surface is reflected by the light incident surface, and the return of the reflected light to the second light-emitting surface is suppressed. Therefore, the influence of the compound resonator, which is formed between the light incident surface and the first light-emitting surface, on the intensity of the light emitted from the second light-emitting surface is suppressed. For this reason, a change in the intensity of the light emitted from the second light-emitting surface can be accurately measured in response to the intensity of the light fed back to the first light-emitting surface. Accordingly, the analysis of the fluid can be performed with higher accuracy.

In the fluid analyzer according to the aspect of the disclosure, the light incident surface may be inclined so as to have a positional relationship where an acute angle is formed between the light incident surface and the second light-emitting surface, and may be inclined so as to form a right angle together with an imaginary plane perpendicular to the surface of the substrate and parallel to the predetermined direction, and so as to form an angle of 45° or more together with the surface of the substrate. According to the fluid analyzer of the aspect of the disclosure, since it is possible to sufficiently suppress the reflection of the light, which is emitted from the second light-emitting surface, on the light incident surface, it is possible to efficiently introduce the light, which is emitted from the second light-emitting surface, into the quantum cascade detector. Accordingly, it is possible to further suppress an influence of the compound resonator, which is formed between the light incident surface and the first light-emitting surface, on the intensity of the light emitted from the second light-emitting surface. The light emitted from the second light-emitting surface can be more reliably absorbed by the quantum cascade detector.

The fluid analyzer according to the aspect of the disclosure may further include a lens disposed between the first light-emitting surface and the inspection region and collimating the light emitted from the first light-emitting surface. According to the fluid analyzer of the aspect of the disclosure, since the light is collimated, the length of the optical path of the light up to the optical element from the first light-emitting surface can be easily increased. For this reason, the absorption or scattering of the light, which is caused by the fluid disposed in the inspection region, can be further facilitated. Therefore, the analysis of the fluid can be performed with higher accuracy.

The fluid analyzer according to the aspect of the disclosure may further include a multi-path cell including the inspection region in the multi-path cell. According to the fluid analyzer of the aspect of the disclosure, the length of the optical path of the light in the inspection region is increased by the multi-path cell. For this reason, a change in the intensity of the light, in a case in which the fluid to be analyzed is disposed in the inspection region, can be made to become more significant.

In the fluid analyzer according to the aspect of the disclosure, the quantum cascade detector may include a light reflecting surface facing the light incident surface in the predetermined direction, and a reflective film reflecting light emitted from the second light-emitting surface, may be formed on the light reflecting surface. According to the fluid analyzer of the aspect of the disclosure, since light present in the quantum cascade detector is reflected by the reflective film, the light is hard to be emitted to the outside of the quantum cascade detector. For this reason, light can be further absorbed in the quantum cascade detector.

According to an aspect of the disclosure, it is possible to provide a fluid analyzer that can analyze a fluid to be analyzed with high sensitivity and high accuracy.

DETAILED DESCRIPTION

Figure 1:
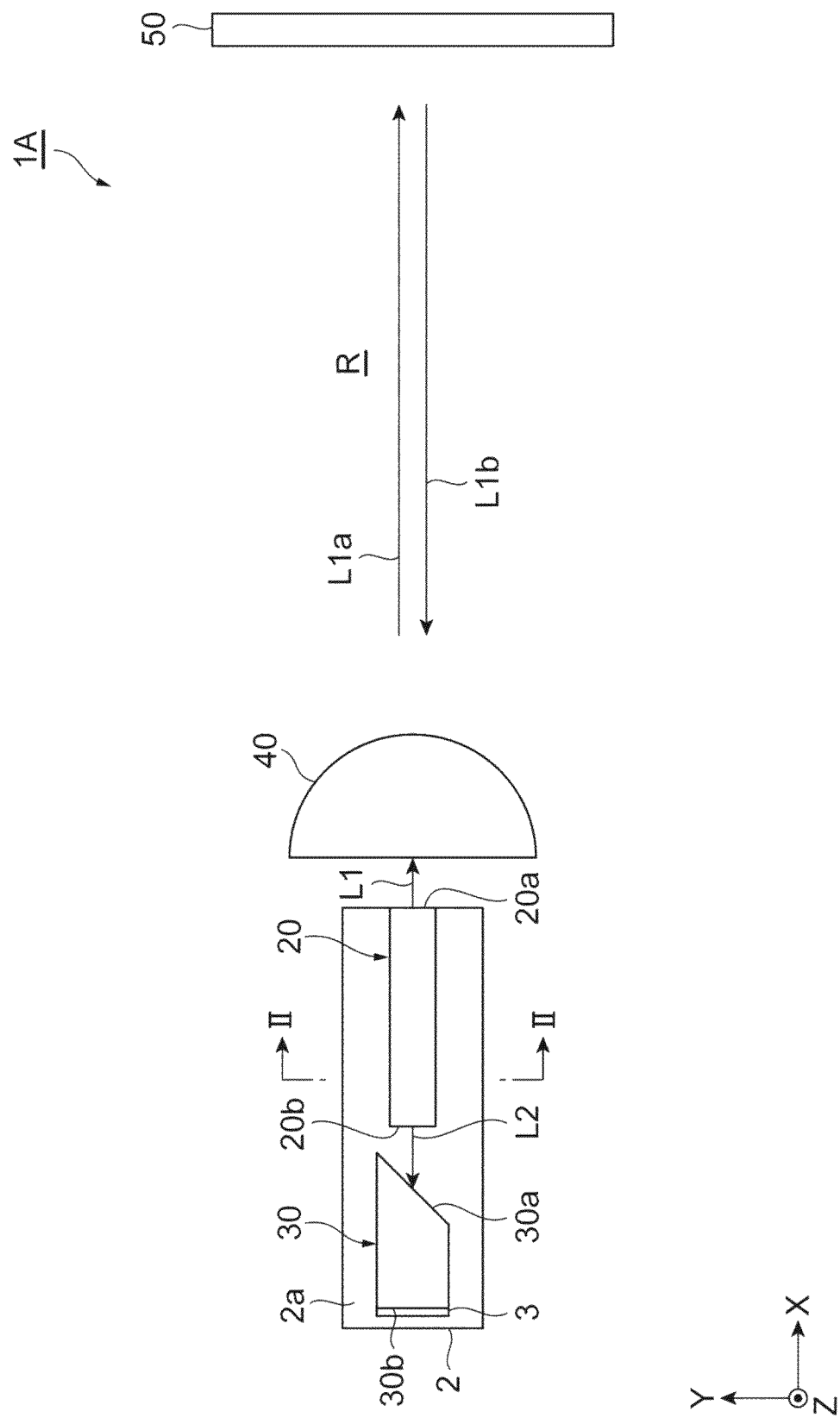
FIG. 1 is a schematic plan view of a fluid analyzer according to a first embodiment of the disclosure.

Embodiments of the disclosure will be described in detail below with reference to the drawings. Meanwhile, the same portions or corresponding portions will be denoted in the respective drawings by the same reference numerals and the repeated description thereof will be omitted.

First Embodiment

As illustrated in FIG. 1, a fluid analyzer 1A includes a substrate 2, a quantum cascade laser 20 (hereinafter, referred to as a "QCL 20"), a quantum cascade detector 30 (hereinafter, referred to as a "QCD 30"), a lens 40, and a reflective member (optical element) 50.

The substrate 2 is made of, for example, a semi-insulating semiconductor material, such as InP. When being viewed in a Z-axis direction, the width of the substrate 2 in a Y-axis direction is, for example, about several hundred µm and the length of the substrate 2 in an X-axis direction (a predetermined direction parallel to a surface 2a of the substrate 2) is, for example, about several mm. The Z-axis direction is a direction perpendicular to the surface 2a of the substrate 2. The Y-axis direction is a direction perpendicular to the Z-axis direction. The X-axis direction is a direction perpendicular to the Z-axis direction and the Y-axis direction.

Figure 2:
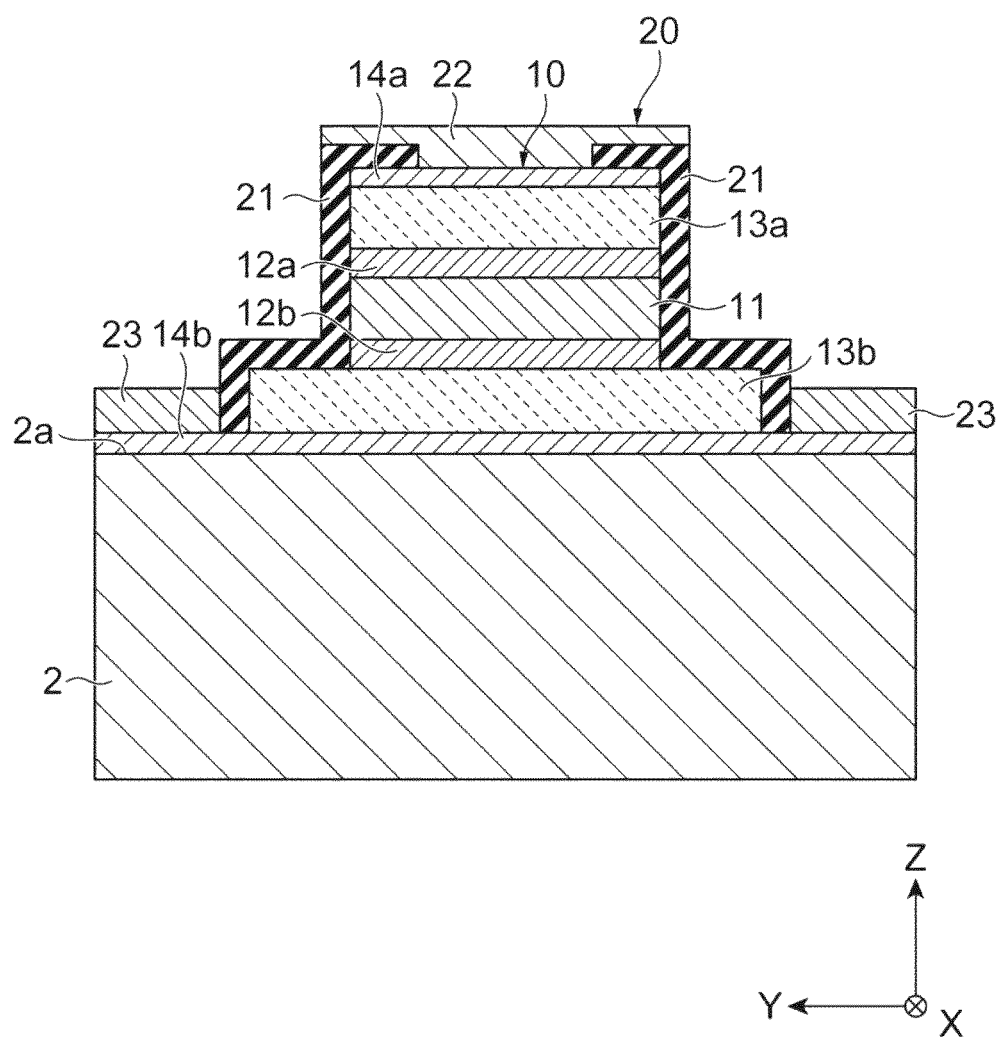
FIG. 2 is a cross-sectional view taken along line II-II of FIG. 1.

The QCL 20 is formed on the surface 2a of the substrate 2. The width of the QCL 20 in the Y-axis direction is in the range of, for example, about several µm to several tens µm. The length of the QCL 20 in the X-axis direction is, for example, about several mm. As illustrated in FIG. 2, the QCL 20 includes a layer structure 10.

The layer structure 10 is a ridge stripe structure that includes an active layer 11, an upper guide layer 12a and a lower guide layer 12b, an upper clad layer 13a and a lower clad layer 13b, and an upper contact layer 14a and a lower contact layer 14b. The lower contact layer 14b is made of, for example, InGaAs and is formed on the surface 2a of the substrate 2. The lower clad layer 13b is made of, for example, InP and is formed on the lower contact layer 14b. The lower guide layer 12b is made of, for example, InGaAs and is formed on the lower clad layer 13b. The active layer 11 has a quantum cascade structure and is formed on the lower guide layer 12b. The upper guide layer 12a is made of, for example, InGaAs and is formed on the active layer 11. The upper clad layer 13a is made of, for example, InP and is formed on the upper guide layer 12a. The upper contact layer 14a is made of, for example, InGaAs and is formed on the upper clad layer 13a. The layer structure 10 is sequentially epitaxially grown by, for example, molecular beam epitaxy, organometallic vapor-phase epitaxy, or the like.

An example of the quantum cascade structure of the active layer 11 per cycle is shown in Table 1. In the quantum cascade structure of the active layer 11, for example, the quantum cascade structures of Table 1 are repeated 35 cycles and are subjected to cascade connection.

TABLE 1

| | Semiconductor layer | Composition | Thickness (nm) | Doping |
|---|---|---|---|---|
| Absorption/light-emitting region | Barrier layer 1 | AlInAs | 2.7 | undoped |
| | Well layer 1 | InGaAs | 2.1 | undoped |
| | Barrier layer 2 | AlInAs | 0.9 | undoped |
| | Well layer 2 | InGaAs | 6.1 | undoped |
| Transport/injection region | Barrier layer 3 | AlInAs | 1.4 | undoped |
| | Well layer 3 | InGaAs | 5.2 | undoped |
| | Barrier layer 4 | AlInAs | 1.4 | undoped |
| | Well layer 4 | InGaAs | 4.4 | undoped |
| | Barrier layer 5 | AlInAs | 1.4 | undoped |
| | Well layer 5 | InGaAs | 4.0 | undoped |
| | Barrier layer 6 | AlInAs | 1.6 | undoped |

TABLE 1-continued

| Semiconductor layer | Composition | Thickness (nm) | Doping |
|---|---|---|---|
| Well layer 6 | InGaAs | 3.9 | undoped |
| Barrier layer 7 | AlInAs | 1.8 | Si doped $2 \times 10^{17}$ cm$^{-3}$ |
| Well layer 7 | InGaAs | 3.7 | Si doped $2 \times 10^{17}$ cm$^{-3}$ |
| Barrier layer 8 | AlInAs | 2.0 | Si doped $2 \times 10^{17}$ cm$^{-3}$ |
| Well layer 8 | InGaAs | 3.3 | Si doped $2 \times 10^{17}$ cm$^{-3}$ |
| Barrier layer 9 | AlInAs | 2.1 | undoped |
| Well layer 9 | InGaAs | 2.8 | undoped |
| Barrier layer 10 | AlInAs | 1.7 | undoped |
| Well layer 10 | InGaAs | 2.8 | undoped |

In the QCL 20, the width of the lower contact layer 14b in the Y-axis direction is equal to the width of the substrate 2 in the Y-axis direction. The width of each of the lower clad layer 13b, the lower guide layer 12b, the active layer 11, the upper guide layer 12a, the upper clad layer 13a, and the upper contact layer 14a in the Y-axis direction is smaller than the width of the substrate 2 in the Y-axis direction. Accordingly, both edge portions of the lower contact layer 14b in the Y-axis direction protrude to both sides in the Y-axis direction from both side surfaces of each of the lower clad layer 13b, the lower guide layer 12b, the active layer 11, the upper guide layer 12a, the upper clad layer 13a, and the upper contact layer 14a in the Y-axis direction.

An insulating film 21 made of, for example, SiN is formed on each of both side surfaces of the lower clad layer 13b, the lower guide layer 12b, the active layer 11, the upper guide layer 12a, the upper clad layer 13a, and the upper contact layer 14a in the Y-axis direction. An upper electrode 22 made of, for example, Au is formed on the upper contact layer 14a. A lower electrode 23 made of, for example, Au is formed on each of both edge portions of the lower contact layer 14b in the Y-axis direction.

As illustrated in FIG. 1, the QCL 20 includes a first light-emitting surface 20a and a second light-emitting surface 20b that face each other in the X-axis direction.

The first light-emitting surface 20a is one end face of the QCL 20 in the X-axis direction. The first light-emitting surface 20a is parallel to a Y-Z plane perpendicular to the X-axis direction. The first light-emitting surface 20a is a cut surface, such as a cleavage surface, at the time of, for example, dicing. The first light-emitting surface 20a reflects a part of a laser beam L1 emitted from the first light-emitting surface 20a, and transmits the rest of the laser beam L1.

The second light-emitting surface 20b is the other end face of the QCL 20 in the X-axis direction. The second light-emitting surface 20b is parallel to the Y-Z plane perpendicular to the X-axis direction. The second light-emitting surface 20b is formed using, for example, a photolithographic technique and a dry etching technique. The second light-emitting surface 20b reflects a part of a laser beam L2 emitted from the second light-emitting surface 20b, and transmits the rest of the laser beam L2. In this embodiment, an optical resonator is formed between the first light-emitting surface 20a and the second light-emitting surface 20b. That is, the QCL 20 is formed as a Fabry-Perot element oscillating in a multi-mode.

The QCD 30 is formed on the surface 2a of the substrate 2. The QCD 30 is positioned on the other side of the QCL 20 in the X-axis direction. The width of the QCD 30 in the Y-axis direction is, for example, about several tens μm (for example, 50 μm), and the length of the QCD 30 in the X-axis direction is in the range of, for example, about several hundred μm to several mm (for example, 500 μm).

The QCD 30 includes the same layer structure 10 as the QCL 20, and the active layer 11 of the QCD 30 has the same quantum cascade structure as the active layer 11 of the QCL 20. The QCD 30 includes an insulating film, an upper electrode, and a lower electrode (each of which is not illustrated), which correspond to the insulating film 21, the upper electrode 22, and the lower electrode 23 of the QCL 20, instead of the insulating film 21, the upper electrode 22, and the lower electrode 23 of the QCL 20.

The QCD 30 includes a light incident surface 30a and a light reflecting surface 30b that face each other in the X-axis direction.

The light incident surface 30a is one end face of the QCD 30 in the X-axis direction. The light incident surface 30a faces the second light-emitting surface 20b of the QCL 20 in the X-axis direction. The light incident surface 30a is inclined so as to have a positional relationship where an acute angle is formed between the light incident surface 30a and the second light-emitting surface 20b. For example, the light incident surface 30a is inclined so as to form a right angle together with an X-Y plane perpendicular to the Z-axis direction and so as to form an angle of 45° together with the Y-Z plane perpendicular to the X-axis direction. Accordingly, since light, which is reflected by the light incident surface 30a, of the laser beam L2 becomes return light, the incidence of the return light on the second light-emitting surface 20b is suppressed. The light incident surface 30a is formed using, for example, a photolithographic technique and a dry etching technique. A distance between the light incident surface 30a and the second light-emitting surface 20b is, for example, about several tens μm. In this case, it is very difficult to form an antireflection coating, which is formed of, for example, a dielectric multilayer, on the light incident surface 30a. Inclining the light incident surface 30a is very important to suppress an influence of a compound resonator, which is formed between the light incident surface 30a and the first light-emitting surface 20a, on the intensity of the laser beam L2. Meanwhile, in a case in which the distance between the light incident surface 30a and the second light-emitting surface 20b is, for example, 100 μm or more, the antireflection coating formed of a dielectric multilayer may be formed on the light incident surface 30a and the light incident surface 30a may be parallel to the Y-Z plane perpendicular to the X-axis direction.

The light reflecting surface 30b is the other end face of the QCD 30 in the X-axis direction. The light reflecting surface 30b is parallel to the Y-Z plane. The light reflecting surface 30b is a cut surface, such as a cleavage surface, at the time of, for example, dicing. A highly reflective film 3 is formed on the light reflecting surface 30b. The highly reflective film 3 is, for example, a dielectric multilayer or a metal-deposited film. The highly reflective film 3 inhibits light, which is guided in the QCD 30, from being transmitted through the light reflecting surface 30b and emitted to the outside. The highly reflective film 3 reflects the laser beam L2, which is emitted from the second light-emitting surface 20b and is incident from the light incident surface 30a, with a reflectance of 90% or more.

In the fluid analyzer 1A, the lens 40 and the reflective member 50 are disposed on the optical path of the laser beam L1 emitted from the first light-emitting surface 20a of the QCL 20. An inspection region R in which a fluid (for example, a gas) to be analyzed is to be disposed is provided between the lens 40 and the reflective member 50. A distance between the first light-emitting surface 20a and the reflective member 50 can be properly set in accordance with the intensity of the laser beam L1 output from the QCL 20 and the state of a gas to be analyzed. Meanwhile, "a gas to be analyzed is to be disposed in the inspection region R" includes: a case in which a gas to be analyzed is intentionally disposed using, for example, a gas cell or the like in the inspection region R; and a case in which a gas to be analyzed is present in a space including the inspection region R (for example, a space in which the fluid analyzer 1A is disposed), so that the gas to be analyzed is disposed in the inspection region R.

The lens 40 is disposed between the first light-emitting surface 20a and the inspection region R. The lens 40 collimates the laser beam L1 emitted from the first light-emitting surface 20a of the QCL 20. The lens 40 is, for example, an aspherical lens made of a material that is transparent at an oscillation wavelength (for example, ZnSe, Ge, or the like). A reflection-reducing film (not illustrated), which is formed of a dielectric multilayer, may be provided on each of both surfaces of the lens 40. The reflection-reducing film reduces the reflectance of the laser beam L1 to 1% or less at, for example, the oscillation wavelength of the QCL 20. The lens 40 may be various lenses, such as a plano-convex lens, and may be a compound lens or a parabolic mirror. The lens 40 may be provided so as to be in contact with the first light-emitting surface 20a, and may be formed integrally with the first light-emitting surface 20a.

The reflective member 50 is disposed on the optical path of the laser beam L1 emitted from the first light-emitting surface 20a across the inspection region R. A distance between the lens 40 and the reflective member 50 is in the range of, for example, about several cm to several tens cm (for example, 20 cm). A laser beam L1a, which is collimated by the lens 40, is incident on the reflective member 50 through the inspection region R. The reflective member 50 reflects the incident laser beam L1a to feed return light L1b back to the first light-emitting surface 20a through the inspection region R. The reflective member 50 is, for example, a plane mirror. A metal-deposited film or a dielectric multilayer, which reflects the laser beam L1a with a reflectance of 90% or more, is formed on the reflective member 50. The reflective member 50 may be a concave mirror of which the focal length is longer than the distance between the lens 40 and the reflective member 50. The reflective member 50 may be a corner cube reflector that can reflect the laser beam L1a in the X-axis direction. In this case, since the laser beam L1a is reflected by the corner cube reflector, the alignment of the reflective member 50 is easily performed. The reflective member 50 may be a spatial light modulator (SLM) that can reflect the laser beam L1a in the X-axis direction.

The fluid analyzer 1A adapted as described above is used in the following manner in a state in which the fluid analyzer 1A is mounted on, for example, a wiring board. That is, the fluid analyzer 1A is exposed to a gas atmosphere not including a fluid to be analyzed (here, a gas that absorbs a laser beam oscillated by the QCL 20), and a bias voltage is applied to the QCL 20 through the upper electrode 22 and the lower electrode 23 and a current is thus applied to the QCL 20 in a state in which the gas to be analyzed is not disposed in the inspection region R. As a result, laser oscillation is caused in the QCL 20. Accordingly, the laser beam L1 is emitted from the first light-emitting surface 20a of the QCL 20, and the laser beam L2 is emitted from the second light-emitting surface 20b.

The laser beam L1, which is emitted from the first light-emitting surface 20a of the QCL 20, is collimated by the lens 40. The laser beam L1a is reflected by the reflective member 50 through the inspection region R. The return light L1b is fed back to the first light-emitting surface 20a through the inspection region R. When the return light L1b is fed back to the first light-emitting surface 20a, a laser beam L2 having an intensity corresponding to the intensity of the return light L1b, which is not absorbed or scattered by the gas to be analyzed, is emitted from the second light-emitting surface 20b. The laser beam L2 is incident on the light incident surface 30a.

Since a bias voltage is not applied to the QCD 30 of which the structure of the active layer 11 is the same as the of the QCL 20, the QCD 30 operates as a detector for detecting the laser beam L2 that is incident on the light incident surface 30a. When the laser beam L2 is incident on the light incident surface 30a, a signal is output from the QCD 30 through the upper electrode and the lower electrode. This signal is used as a reference signal for differential optical absorption spectroscopy that is to be performed for the gas to be analyzed. Meanwhile, the reference signal may be stored in a storage unit that is provided in a processing circuit provided on a subsequent stage.

On the other hand, the fluid analyzer 1A is exposed to the atmosphere of the gas to be analyzed, so that the gas to be analyzed is disposed in the inspection region R. In this state, a bias voltage is applied to the QCL 20 through the upper electrode 22 and the lower electrode 23 and a current is thus applied to the QCL 20. As a result, laser oscillation is caused in the QCL 20. Accordingly, a laser beam L1 is emitted from the first light-emitting surface 20a of the QCL 20, and a laser beam L2 is emitted from the second light-emitting surface 20b.

The laser beam L1, which is emitted from the first light-emitting surface 20a of the QCL 20, is collimated by the lens 40. A laser beam L1a is reflected by the reflective member 50 through the gas to be analyzed that is disposed in the inspection region R. A return light L1b is fed back to the first light-emitting surface 20a through the gas to be analyzed. When the return light L1b is fed back to the first light-emitting surface 20a, a laser beam L2 having an intensity corresponding to the intensity of the return light L1b, which is absorbed or scattered by the gas to be analyzed, is emitted from the second light-emitting surface 20b. The laser beam L2 is incident on the light incident surface 30a. The laser beam L2 is incident on the light incident surface 30a of the QCD 30 and a signal is output from the QCD 30 through the upper electrode and the lower electrode.

Here, since the absorption or scattering of the laser beam L1 (the laser beam L1a and the return light L1b), which is caused by the gas, occurs in a case in which the gas to be analyzed is disposed in the inspection region R, a change in the oscillation characteristics of the QCL 20 occurs in response to a change in the intensity of the return light L1b. That is, the intensity of the laser beam L2 emitted from the second light-emitting surface 20b is reduced in comparison with the intensity of the laser beam in a case in which the gas to be analyzed is not disposed in the inspection region R. Accordingly, a difference between the signal output from the QCD 30 and the above-mentioned reference signal is taken in the processing circuit provided on the subsequent stage for the analysis of the gas to be analyzed. In this way, differential optical absorption spectroscopy is performed for the gas to be analyzed through the comparison of the signal output from the QCD 30 with the reference signal.

Figure 3:
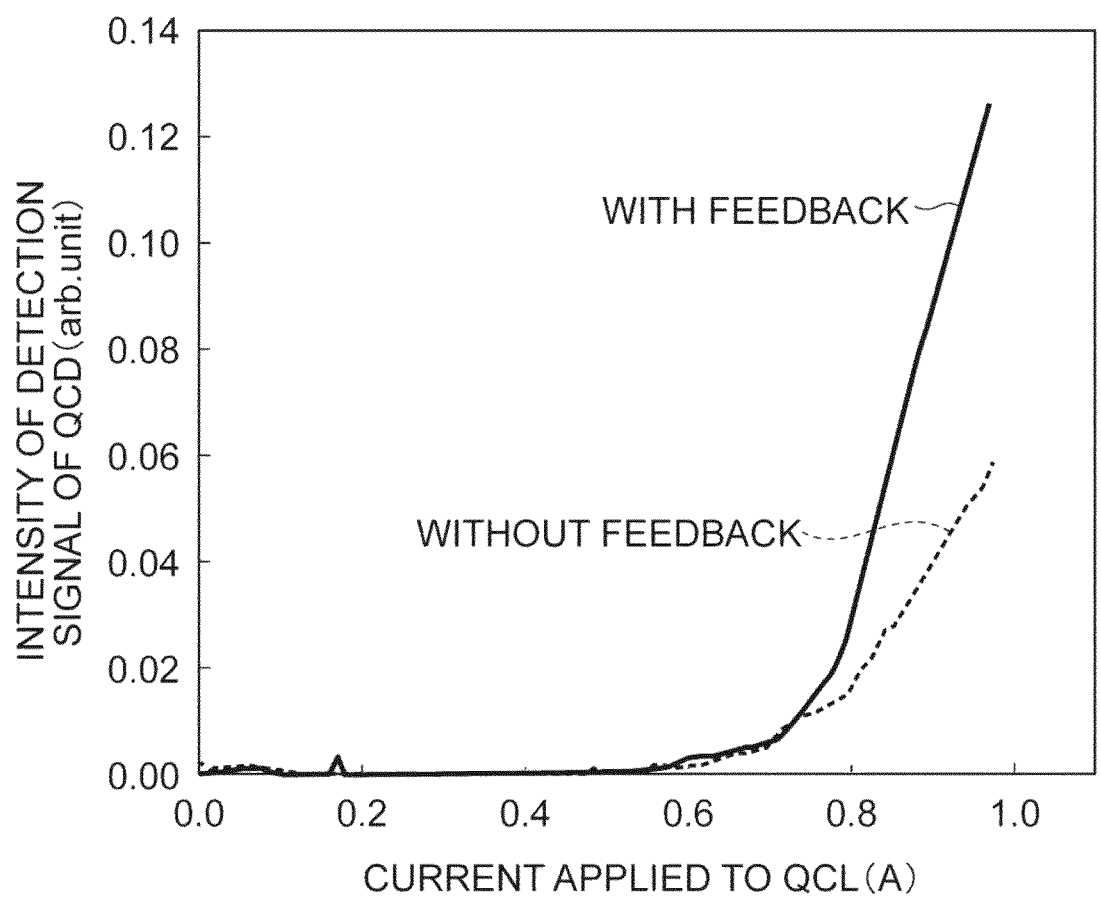
FIG. 3 is a graph illustrating a relationship between a current applied to a QCL of the fluid analyzer of FIG. 1 and the intensity of a detection signal of a QCD.

FIG. 3 is a graph illustrating a relationship between a current applied to the QCL 20 of the fluid analyzer 1A of FIG. 1 and the intensity of a detection signal of the QCD 30. In FIG. 3, a solid line represents the intensity of a detection signal of the QCD 30, which detects the laser beam L2, with respect to a current applied to the QCL 20 in a case in which the laser beam L1a is reflected by the reflective member 50 and is fed back to the first light-emitting surface 20a as the return light L1b. A broken line represents the intensity of a detection signal of the QCD 30 with respect to a current applied to the QCL 20 in a case in which the laser beam L1a is not reflected by the reflective member 50 (the return light L1b is not fed back to the first light-emitting surface 20a). In an example of FIG. 3, an aspherical lens, which has a focal length of 3 mm and a numerical aperture of 0.85 and is made of ZnSe, is used as the lens 40 and a plane mirror on which an Au film is formed is used as the reflective member 50. A distance between the lens 40 and the reflective member 50 is set to 20 cm.

In FIG. 3, the intensity of a detection signal of the QCD 30, which detects the laser beam L2 in a case in which the laser beam L1a is not reflected by the reflective member 50, corresponds to the intensity of the laser beam L2 when a change in the oscillation characteristics of the QCL 20 caused by the return light L1b does not occur. The intensity of a detection signal of the QCD 30, which detects the laser beam L2 in a case in which the laser beam L1a is fed back by the reflective member 50, corresponds to the intensity of the laser beam L2 when a change in the oscillation characteristics of the QCL 20 occurs in response to a change in the intensity of the return light L1b. As illustrated in FIG. 3, it is found that the intensity of a detection signal of the QCD 30, which detects the laser beam L2, (the intensity of the laser beam L2 emitted from the second light-emitting surface 20b) in a case in which the laser beam L1a is reflected by the reflective member 50 is substantially doubled in a range where a current applied to the QCL 20 is about 0.7 A or more, in comparison with the intensity of the detection signal in a case in which the laser beam L1a is not reflected by the reflective member 50.

Figure 4A:
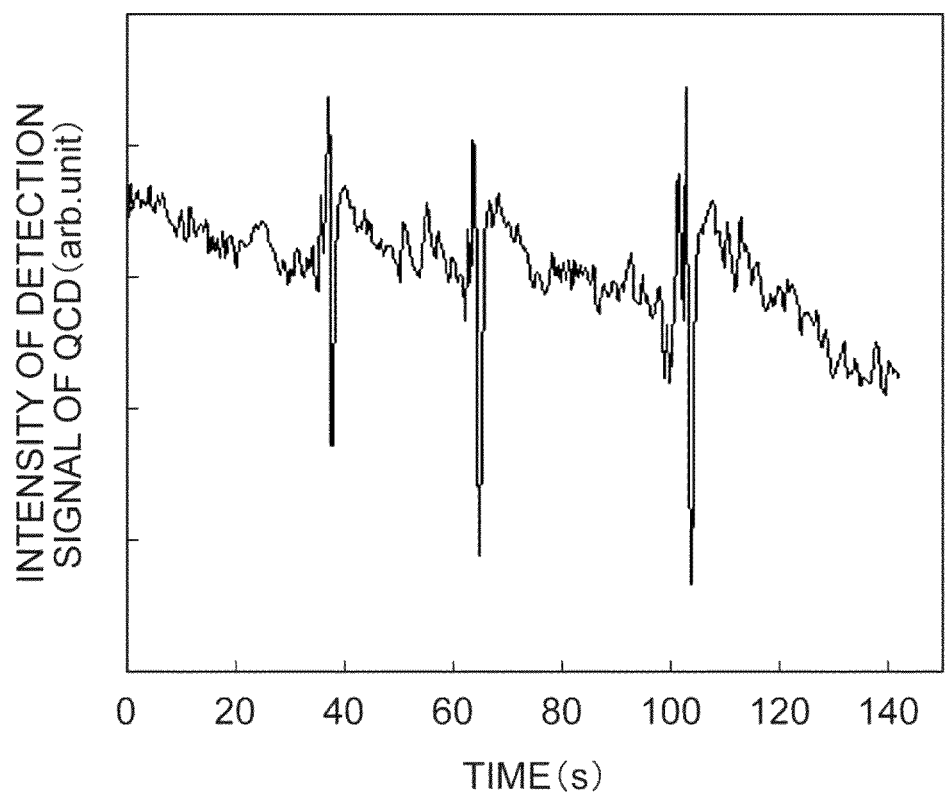
FIG. 4A is a graph illustrating a time change in the intensity of a detection signal of the QCD in a case in which $N_2O$ is ejected onto an optical path of light.

FIG. 4A is a graph illustrating a time change in the intensity of a detection signal of the QCD 30 in a case in which $N_2O$ is ejected onto the optical path of the laser beam L1a. In an example of FIG. 4A, a current applied to the QCL 20 is fixed to a predetermined value. In a state in which the return light L1b is fed back to the first light-emitting surface 20a and the laser beam L2 is continuously detected by the QCD 30, $N_2O$ is ejected onto the optical path of the laser beam L1a at a predetermined timing. $N_2O$ is a gas that easily absorbs the laser beam L1a oscillated by the QCL 20 here. As illustrated in FIG. 4A, at a timing where $N_2O$ is ejected, the intensity of the return light L1b is changed and a change in the oscillation characteristics of the QCL 20 occurs. As a result, the intensity of a detection signal of the QCD 30, which detects the laser beam L2, is significantly reduced. Accordingly, it is found that a fact that a gas (here, $N_2O$) absorbing the laser beam L1 (the laser beam L1a and the return light L1b) is disposed in the inspection region R is indicated as a reduction in the intensity of a detection signal of the QCD 30 detecting the laser beam L2.

Figure 4B:
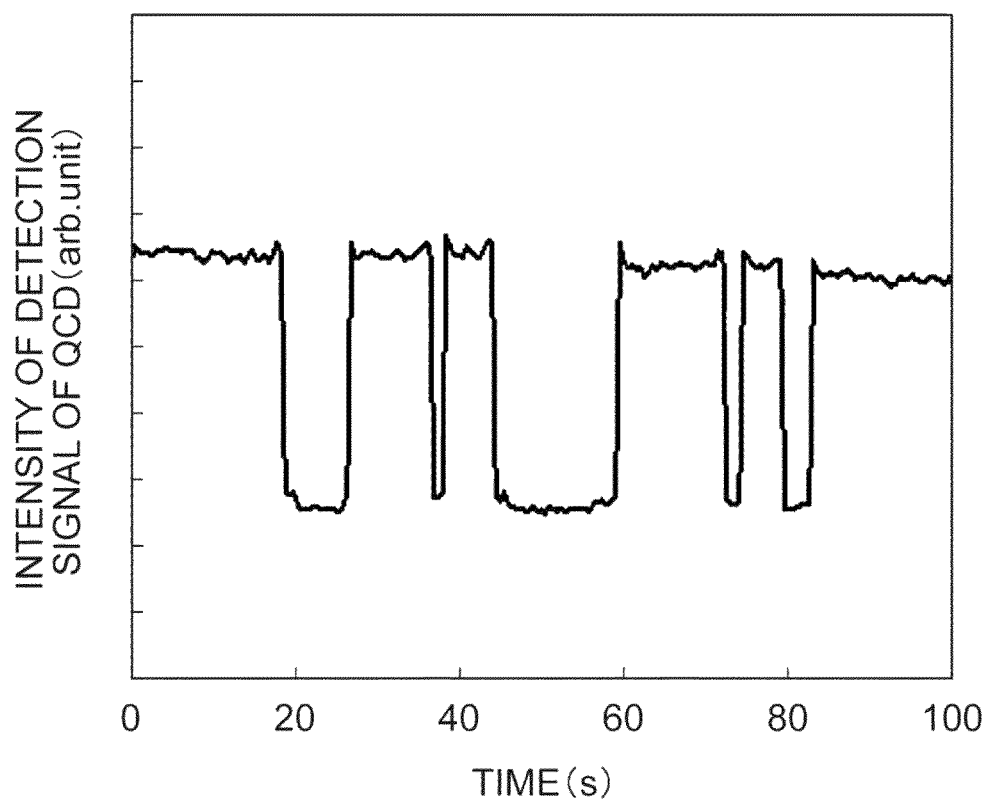
FIG. 4B is a graph illustrating a time change in the intensity of a detection signal of the QCD in a case in which the optical path of light is physically blocked.

FIG. 4B is a graph illustrating a time change in the intensity of a detection signal of the QCD 30 in a case in which the optical path of the laser beam L1a is physically blocked. In an example of FIG. 4B, the optical path of the laser beam L1a is physically blocked at a predetermined timing by an object, such as paper, in a state in which the laser beam L2 is continuously detected by the QCD 30. As illustrated in FIG. 4B, the intensity of the return light L1b is changed and a change in the oscillation characteristics of the QCL 20 occurs at a timing or a period where the optical path of the laser beam L1a is blocked. As a result, the intensity of a detection signal of the QCD 30, which detects the laser beam L2, is significantly reduced. Accordingly, it is found that a fact that an object changing the intensity of the return light L1b is disposed in the inspection region R is indicated as a reduction in the intensity of a detection signal of the QCD 30 detecting the laser beam L2.

As described above, in the fluid analyzer 1A, a laser beam L1 emitted from the first light-emitting surface 20a is reflected by the reflective member 50 and a reflected return light L1b is fed back to the first light-emitting surface 20a. When the return light L1b is fed back to the first light-emitting surface 20a, a laser beam L2 having an intensity corresponding to the intensity of the return light L1b, which is fed back to the first light-emitting surface 20a, is emitted from the second light-emitting surface 20b. Since the absorption or scattering of the laser beam L1, which is caused by the gas, occurs in a case in which the gas to be analyzed is disposed in the inspection region R, the intensity of the laser beam L2 is changed in comparison with the intensity of the laser beam in a case in which the gas is not disposed in the inspection region R. Here, the laser beam L2 emitted from the second light-emitting surface 20b is a laser beam that is oscillated from the second light-emitting surface 20b as an end face of the optical resonator and has an intensity corresponding to the intensity of the return light L1b fed back to the first light-emitting surface 20a. For this reason, a change in the intensity of the laser beam L2 is likely to become more significant than a change in the electrical characteristics of the QCL 20 in response to the intensity of the return light L1b fed back to the first light-emitting surface 20a. Accordingly, it is possible to measure a change in the intensity of the return light L1b fed back to the first light-emitting surface 20a, while inhibiting sensitivity and accuracy from depending on the influence of external factors, by measuring a change in the intensity of the laser beam L2 emitted from the second light-emitting surface 20b by the QCD 30. Therefore, according to the fluid analyzer 1A, the fluid to be analyzed can be analyzed with high sensitivity and high accuracy.

In the fluid analyzer 1A, an optical resonator is formed between the first light-emitting surface 20a and the second light-emitting surface 20b. Accordingly, the QCL 20 functions as an optical resonator oscillating laser. For this reason, it is possible to perform the analysis (so-called monitoring) of the presence of the gas in the inspection region R with high sensitivity and high accuracy by setting the oscillation wavelength of the QCL 20 in response to the kind of the gas to be analyzed.

In the fluid analyzer 1A, the QCL 20 is formed as a Fabry-Perot element oscillating in a multi-mode. Accordingly, since light, which is broader than light obtained in a single mode, is emitted from the first light-emitting surface 20a of the QCL 20, various gases can be analyzed as an object to be analyzed. Further, since the oscillation of the QCL 20 and the detection of the laser beam L2 performed by the QCD 30 are hard to be affected by a position at which the reflective member 50 is disposed, the degree of freedom of the layout of the reflective member 50 is improved and the QCL 20 and the reflective member 50 are easily aligned with each other.

In the fluid analyzer 1A, the light incident surface 30a is inclined so as to have a positional relationship where an acute angle is formed between the light incident surface 30a and the second light-emitting surface 20b. Accordingly, the laser beam L2 emitted from the second light-emitting surface 20b is reflected by the light incident surface 30a, and the return of the reflected laser beam L2 to the second light-emitting surface 20b is suppressed. Therefore, the influence of the compound resonator, which is formed between the light incident surface 30a and the first light-emitting surface 20a, on the intensity of the laser beam L2 emitted from the second light-emitting surface 20b is suppressed. For this reason, a change in the intensity of the laser beam L2 emitted from the second light-emitting surface 20b can be accurately measured in response to the intensity of the return light L1b fed back to the first light-emitting surface 20a. Accordingly, the analysis of a fluid can be performed with higher accuracy.

The fluid analyzer 1A further includes the lens 40 that is disposed between the first light-emitting surface 20a and the inspection region R and collimates the laser beam L1 emitted from the first light-emitting surface 20a. Accordingly, since the laser beam L1 is collimated, the length of the optical path of the laser beam L1a and the return light L1b up to the reflective member 50 from the first light-emitting surface 20a can be easily increased. For this reason, the absorption or scattering of the laser beam L1a and the return light L1b, which is caused by the gas disposed in the inspection region R, can be further facilitated. Therefore, the analysis of a fluid can be performed with higher accuracy.

In the fluid analyzer 1A, the QCD 30 includes the light reflecting surface 30b facing the light incident surface 30a in the X-axis direction, and the highly reflective film 3, which reflects the laser beam. L2 emitted from the second light-emitting surface 20b, is formed on the light reflecting surface 30b. Accordingly, since light present in the QCD 30 is reflected by the highly reflective film 3, the light is hard to be emitted to the outside of the QCD 30. For this reason, light can be further absorbed in the QCD 30.

Second Embodiment

Figure 5:
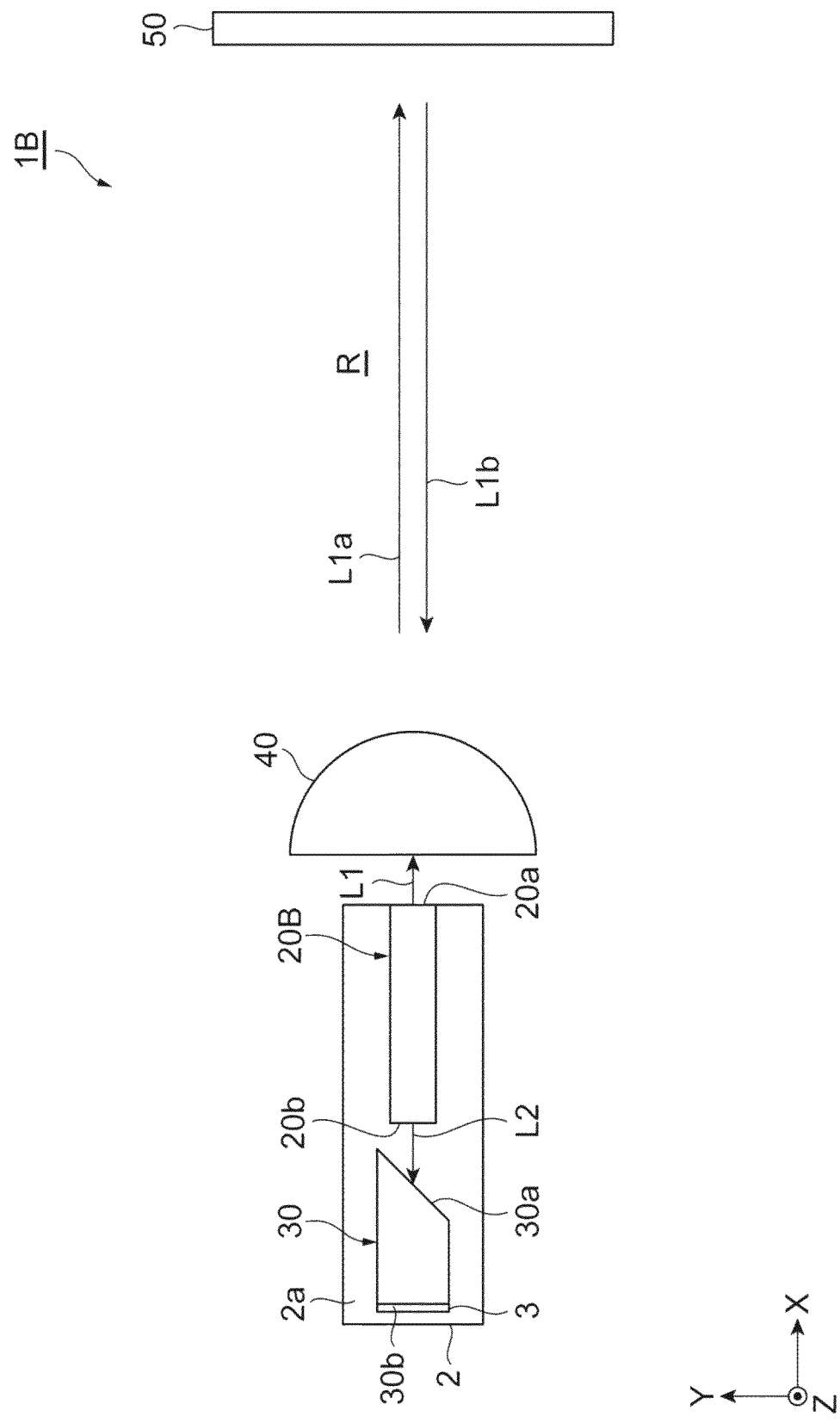
FIG. 5 is a schematic plan view of a fluid analyzer according to a second embodiment of the disclosure.

As illustrated in FIG. 5, a fluid analyzer 1B is mainly different from the above-mentioned fluid analyzer 1A in that the fluid analyzer 1B includes a quantum cascade laser 20B (hereinafter, referred to as a "QCL 20B") instead of the QCL 20 and the length of the optical path of the laser beam L1 (the laser beam L1a and the return light L1b) up to the reflective member 50 from the first light-emitting surface 20a of the QCL 20B (hereinafter, simply referred to as "the length of the optical path of the laser beam L1" in this embodiment) is the integer multiple of a half of the oscillation wavelength of the QCL 20B.

The structure of the QCL 20B is basically the same as the structure of the QCL 20. The QCL 20B is different from the QCL 20 in that the QCL 20B includes a diffraction grating layer provided on the layer structure 10 and is formed as a distributed feedback (DFB) element. The QCL 20B oscillates in a single mode. The oscillation wavelength of the QCL 20B can be arbitrarily selected in the range of the gain of the QCL 20B. The oscillation wavelength of the QCL 20B may be the wavelength of light that is easily absorbed or scattered by a gas to be analyzed. Accordingly, since the quality of the laser beam L1a collimated by the lens 40 is improved, the length of the optical path of the laser beam L1 can be set to a longer length. Further, since the diameter of the return light L1b on the lens 40 is reduced, the efficiency of coupling of the lens 40 and the QCL 20B is improved and the intensity of the returns light L1b fed back to the first light-emitting surface 20a is increased.

The length of the optical path of the laser beam L1 is the integer multiple of a half of the oscillation wavelength of the QCL 20B. To make the length of the optical path of the laser beam L1 be the integer multiple of a half of the oscillation wavelength, the position of the reflective member 50 may be controlled with high accuracy by, for example, a piezoelectric actuator or the like and the oscillation wavelength may be finely adjusted in response to a change in the temperature of the QCL 20B. Accordingly, self-interference where light, which is fed back to the first light-emitting surface 20a as the return light L1b and is incident on the QCL 20B, and light present in the QCL 20B interfere (resonate) with each other occurs. Since the oscillation characteristics of the optical resonator are significantly affected with this interfere, a change in the intensity of the laser beam L2 emitted from the second light-emitting surface 20b becomes significant.

The length of the optical path of the laser beam L1 is set in response to, for example, analytical performance (sensitivity) that is required for the fluid analyzer 1B. The length of the optical path of the laser beam L1 may be 50 cm or less in a case in which a plane mirror is used as the reflective member 50. For example, in a case in which the length of the optical path of the laser beam L1 is set to a length longer than 50 cm, an influence, which is generated in a case in which the laser beam L1a collimated by the lens 40 is spread due to Fresnel diffraction, cannot be ignored even though the QCL 20B oscillates in a single mode. In this case, a concave mirror having a predetermined curvature may be used as the reflective member 50 instead of the plane mirror.

In the fluid analyzer 1B adapted as described above, differential optical absorption spectroscopy is performed for a gas to be analyzed in the same manner as the fluid analyzer 1A in a state in which the oscillation wavelength of the QCL 20B is set to the wavelength of light, which is easily absorbed or scattered by the gas to be analyzed, and the laser output of the QCL 20B (a current applied to the QCL 20B) is fixed.

According to the fluid analyzer 1B, as described above, when the oscillation wavelength of the QCL 20B is set to be equal to the wavelength of light absorbed or scattered by the gas in a case in which, for example, the kind of a gas to be analyzed is specified in advance, the intensity of the return light L1b fed back to the first light-emitting surface 20a can be significantly changed in a case in which the gas is disposed in the inspection region R. Accordingly, the intensity of the laser beam L2 emitted from the second light-emitting surface 20b can be more significantly changed. Further, the length of the optical path of the laser beam L1a and the return light L1b (the length of the optical path of the laser beam L1) up to the reflective member 50 from the first light-emitting surface 20a is the integer multiple of a half of the oscillation wavelength. Accordingly, light, which is fed back to the first light-emitting surface 20a as the return light L1b and is incident on the QCL 20B, and light present in the QCL 20B interfere with each other. Since the oscillation characteristics of the optical resonator are significantly affected with this interference, a change in the intensity of the laser beam L2 emitted from the second light-emitting surface 20b becomes significant. Accordingly, the analysis of the fluid can be performed with higher sensitivity. Particularly, according to the fluid analyzer 1B, it is possible to perform the analysis (so-called monitoring) of the presence of the gas in the inspection region R with high sensitivity and high accuracy by setting the oscillation wavelength of the QCL 20 in response to the kind of the gas to be analyzed. Further, it is expected that the fluid analyzer 1B can also be used for, for example, a range finder, a step profiler, and a speedometer.

Third Embodiment

Figure 6:
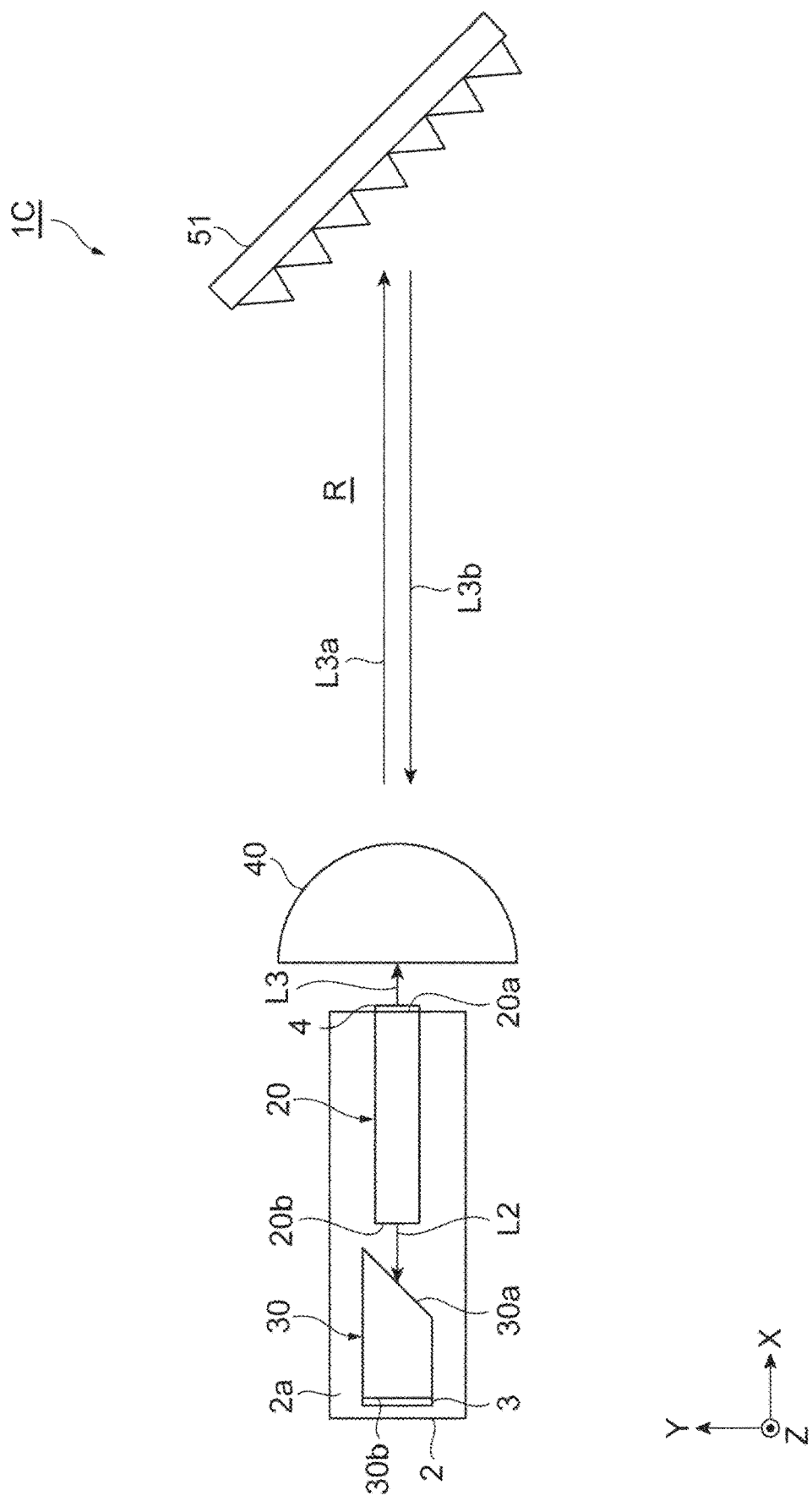
FIG. 6 is a schematic plan view of a fluid analyzer according to a third embodiment of the disclosure.

As illustrated in FIG. 6, a fluid analyzer 1C is mainly different from the above-mentioned fluid analyzer 1A in that the fluid analyzer 1C includes a diffraction grating 51 instead of the reflective member 50 and a reflection-reducing film 4 is formed on the first light-emitting surface 20a.

The diffraction grating 51 diffracts and reflects a laser beam L3 that is emitted from the first light-emitting surface 20a. The diffraction grating 51 is, for example, a blazed diffraction grating of which the cross-section of each grating has a saw-tooth shape. A laser beam L3a, which is collimated by the lens 40, is incident on the diffraction grating 51. The diffraction grating 51 is formed as, for example, a MEMS device oscillating about a Z axis. The diffraction grating 51 is driven so that the direction of the grating surface of the diffraction grating 51 is changed at high speed. The diffraction grating 51 reflects a laser beam L3b, which has a wavelength corresponding to the cycle of grooves of the diffraction grating 51 and the incident angle of the laser beam L3a on the diffraction grating 51, of the laser beam L3a. The diffraction grating 51 is driven so as to feed the laser beam L3b, which has the wavelength, back to the first light-emitting surface 20a. Accordingly, since the incident angle of the laser beam L3a on the diffraction grating 51 can be changed at high speed, the wavelength sweep (scan) of the laser beam L3b, which is fed back to the first light-emitting surface 20a from the diffraction grating 51, can be performed at high speed. Practically, a distance between the first light-emitting surface 20a and the diffraction grating 51 is in the range of, for example, 10 cm to 20 cm. Accordingly, a wavelength resolution in the selection of a wavelength on the diffraction grating 51 is improved.

The reflection-reducing film 4 reduces a reflectance when the laser beam L3 is emitted to the outside from the first light-emitting surface 20a. The reflection-reducing film 4 reflects a part of the laser beam L3 emitted from the first light-emitting surface 20a, and transmits the rest of the laser beam L3. The reflection-reducing film 4 reflects the laser beam L3 with a reflectance of, for example, 10% or less when the laser beam L3 is emitted to the outside from the first light-emitting surface 20a.

A Littrow external resonator (optical resonator) is formed between the second light-emitting surface 20b and the diffraction grating 51. The external resonator oscillates in a single mode with a wavelength, which corresponds to the incident angle of the laser beam L3a on the diffraction grating 51, as a resonant wavelength. Since the laser beam L3b, which is reflected by the diffraction grating 51, is light present in the external resonator, the laser beam L3b does not cause self-interference in the external resonator unlike return light incident from the outside of the external resonator. For this reason, wavelength sweep for scanning a wavelength in a state in which a single mode is maintained can be easily performed in the external resonator. Meanwhile, the structure of the external resonator is not limited to a Littrow type, and may be a Littman type.

In the fluid analyzer 1C adapted as described above, when the fluid analyzer 1C is exposed to a gas atmosphere including the gas to be analyzed, a state in which a gas to be analyzed is disposed in the inspection region R positioned in the external resonator is made. In this state, a bias voltage is applied to the QCL 20 through the upper electrode 22 and the lower electrode 23 and a current is thus applied to the QCL 20. As a result, spontaneous emission light is emitted from the first light-emitting surface 20a of the QCL 20. The spontaneous emission light, which is emitted from the first light-emitting surface 20a of the QCL 20, is collimated by the lens 40. The light, which is collimated by the lens 40, is diffracted and reflected by the diffraction grating 51 through the inspection region R. Light, which has a wavelength corresponding to the cycle of grooves of the diffraction grating 51 and the incident angle of the light on the diffraction grating 51, of the collimated light is reflected by the diffraction grating 51 and is fed back to the first light-emitting surface 20a through the inspection region R. Here, in a case in which the intensity of the light, which is fed back to the first light-emitting surface 20a, exceeds a predetermined threshold value due to an increase in the current applied to the QCL 20, and the like, laser oscillation is caused in the optical resonator formed the second light-emitting surface 20b and the diffraction grating 51. A laser beam L2 is emitted from the second light-emitting surface 20b in a case in which laser oscillation is caused in the optical resonator. The laser beam L2 is incident on the light incident surface 30a. The laser beam L2 is incident on the light incident surface 30a of the QCD 30, and a signal is output from the QCD 30 through the upper electrode and the lower electrode.

Here, since the diffraction grating 51 is driven so that the direction of the grating surface of the diffraction grating 51 is changed, the wavelength sweep (scan) of the laser beam L3b, which is fed back to the first light-emitting surface 20a from the diffraction grating 51, is performed. Accordingly, a reduction occurs in the intensity of the laser beam L3b at a wavelength where the laser beam L3a and the laser beam L3b are absorbed or scattered by a gas disposed in the inspection region R, so that a change occurs in the oscillation characteristics of the QCL 20. That is, the intensity of the laser beam L2 emitted from the second light-emitting surface 20b is reduced in comparison with the intensity of the laser beam L2 in a case in which the laser beam L3a and the laser beam L3b are not absorbed or scattered by the gas disposed in the inspection region R. Accordingly, a difference between a signal output from the QCD 30 and a signal (reference signal), which is obtained in a case in which the laser beam. L3a and the laser beam L3b are not absorbed or scattered by the gas disposed in the inspection region R, is taken in the processing circuit provided on the subsequent stage for the analysis of the gas to be analyzed. In this way, differential optical absorption spectroscopy is performed for the gas to be analyzed through the comparison of the signal output from the QCD 30 with the reference signal. Particularly, according to the fluid analyzer 1C, it is possible to perform the analysis (so-called sensing) of the composition of the gas to be analyzed, which is disposed in the inspection region R, while actively changing the oscillation wavelength in a state in which single-mode oscillation is maintained by changing the incident angle on the diffraction grating 51.

According to the fluid analyzer 1C, as described above, an optical resonator is formed between the second light-emitting surface 20b and the diffraction grating 51. The optical resonator oscillates in a single mode with a wavelength, which corresponds to the incident angle of the laser beam L3 emitted from the first light-emitting surface 20a and incident on the diffraction grating 51, as an oscillation wavelength. Accordingly, it is possible to perform the analysis (so-called sensing) of the composition of the gas to be analyzed, which is disposed in the inspection region R, with high sensitivity and high accuracy while actively changing the oscillation wavelength in a state in which single-mode oscillation is maintained by changing the incident angle on the diffraction grating 51. Further, an external resonator-type optical resonator in which the laser beam L3a and the laser beam L3b reciprocate between the second light-emitting surface 20b and the diffraction grating 51 is formed in the fluid analyzer 1C. The inspection region R is present in the optical resonator. For this reason, the laser beam L3a and the laser beam L3b repeatedly reciprocate between the second light-emitting surface 20b and the diffraction grating 51 while the laser beam L3a and the laser beam L3b are absorbed or scattered by the gas to be analyzed. Accordingly, the oscillation characteristics of the optical resonator are directly affected with a change in the intensity of the laser beam L3b present in the optical resonator. For this reason, a change in the intensity of the laser beam L2 emitted from the second light-emitting surface 20b becomes significant in comparison with a change in the intensity of the laser beam L2 in a case in which the inspection region R is present outside the optical resonator. As a result, the analysis of the fluid can be performed with higher sensitivity.

Fourth Embodiment

Figure 7:
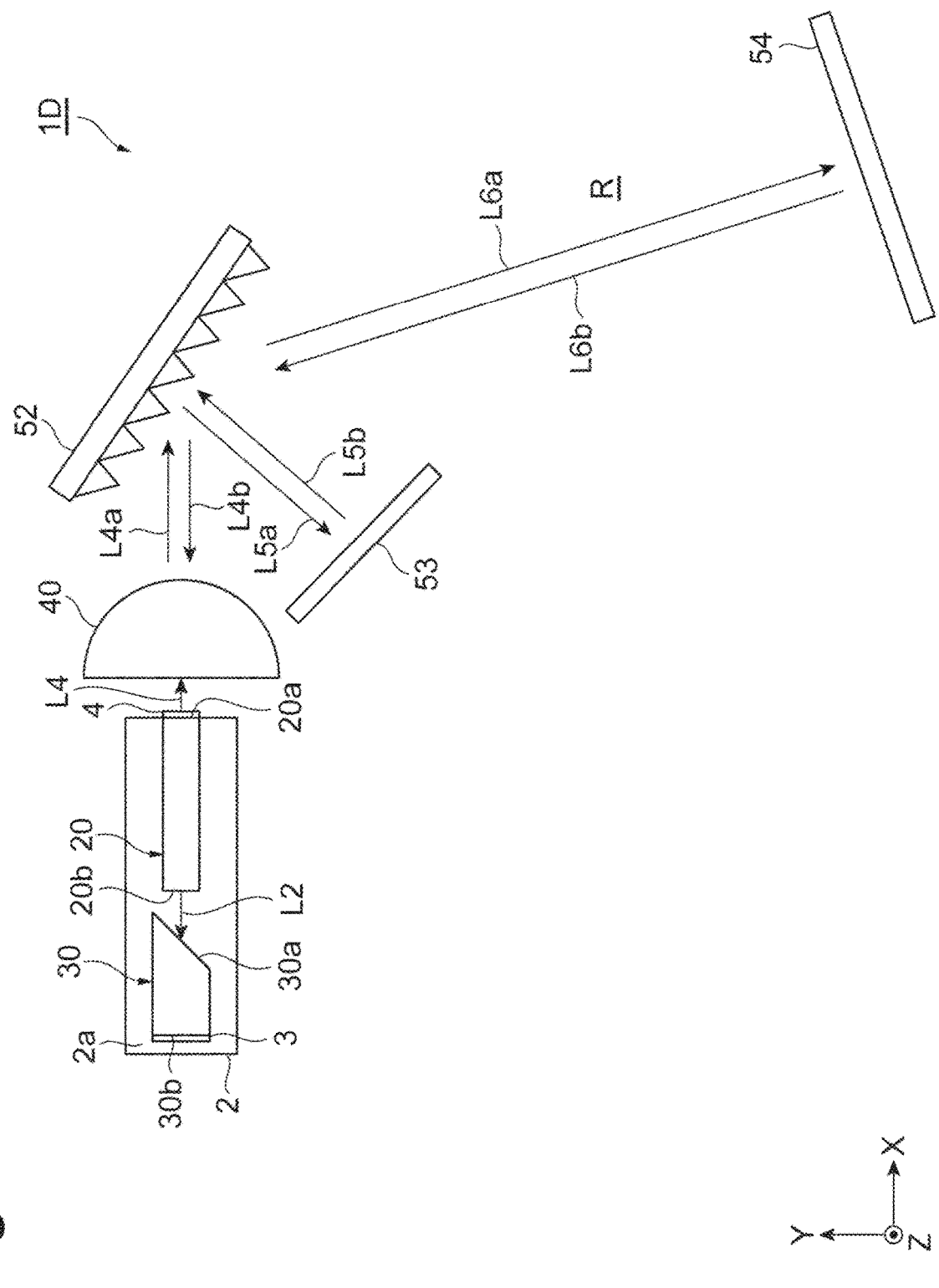
FIG. 7 is a schematic plan view of a fluid analyzer according to a fourth embodiment of the disclosure.

As illustrated in FIG. 7, a fluid analyzer 1D is mainly different from the above-mentioned fluid analyzer 1C in that the fluid analyzer 1D further includes a diffraction grating 52 and a mirror 53 and includes a reflective member 54 instead of the diffraction grating 51.

The diffraction grating 52 diffracts and reflects a laser beam L4 that is emitted from the first light-emitting surface 20a. The diffraction grating 52 is, for example, a blazed diffraction grating of which the cross-section of each grating has a saw-tooth shape. The diffraction grating 52 is disposed on the optical path of a laser beam L4a that is collimated by the lens 40. The laser beam L4a is incident on the diffraction grating 52. The diffraction grating 52 is not formed as a MEMS device unlike the diffraction grating 51, and is fixed so that the incident angle of the laser beam L4a on the diffraction grating 52 is a predetermined angle.

The mirror 53 is disposed on the optical path of a laser beam L5a that is diffracted and reflected by the diffraction grating 52. The laser beam L5a is incident on the mirror 53. The mirror 53 is formed as, for example, a MEMS device oscillating about a Z axis. The mirror 53 is driven so that the direction of the reflective surface of the mirror 53 is changed at high speed. The mirror 53 reflects a laser beam L5b, which has a wavelength corresponding to the incident angle of the laser beam L5a on the mirror 53, of the laser beam L5a. The mirror 53 is driven so as to feed the laser beam L5b, which has the wavelength, back to the first light-emitting surface 20a through the diffraction grating 52 as a laser beam L4b. Accordingly, since the incident angle of the laser beam L5a on the mirror 53 can be changed at high speed, the wavelength sweep (scan) of the laser beam L5b, which is fed back to the first light-emitting surface 20a from the mirror 53, can be performed at high speed.

A Littman external resonator (optical resonator) is formed between the second light-emitting surface 20b and the mirror 53 through the diffraction grating 52. The external resonator oscillates in a single mode with a wavelength, which corresponds to the incident angle of the laser beam L5a on the mirror 53, as a resonant wavelength. The external resonator may be a Littman type in which the deviation of an optical axis caused by wavelength sweep does not occur when a laser beam L6a, which is zero-order reflected light, is used for light output to the reflective member 54. Meanwhile, the structure of the external resonator is not limited to a Littman type, and may be a Littrow type.

The reflective member 54 is disposed on the optical path of the laser beam L6a of light, which is reflected by the diffraction grating 52, across the inspection region R in which a gas to be analyzed is to be disposed. The reflective member 54 reflects the laser beam L6a to feed return light L6b back to the first light-emitting surface 20a through the diffraction grating 52. In the fluid analyzer 1D, the laser beam L6a, which is emitted to the outside from the external resonator, is reflected by the reflective member 54 and returns to the external resonator again.

In the fluid analyzer 1D adapted as described above, when the fluid analyzer 1D is exposed to a gas atmosphere including the gas to be analyzed, a state in which a gas to be analyzed is disposed in the inspection region R is made. In this state, a bias voltage is applied to the QCL 20 through the upper electrode 22 and the lower electrode 23 and a current is thus applied to the QCL 20. As a result, spontaneous emission light is emitted from the first light-emitting surface 20a of the QCL 20. The spontaneous emission light, which is emitted from the first light-emitting surface 20a of the QCL 20, is collimated by the lens 40. The collimated light is diffracted and reflected by the diffraction grating 52. Light, which has a wavelength corresponding to the incident angle on the mirror 53 of the light diffracted and reflected by the diffraction grating 52, is reflected by the mirror 53. Accordingly, the light having the wavelength is fed back to the first light-emitting surface 20a through the diffraction grating 52. Here, in a case in which the intensity of the light, which is fed back to the first light-emitting surface 20a, exceeds a predetermined threshold value due to an increase in the current applied to the QCL 20, and the like, laser oscillation is caused in the optical resonator formed the second light-emitting surface 20b and the mirror 53. In a case in which laser oscillation is caused in the optical resonator, the laser beam L6a is output to the reflective member 54.

The laser beam L6a is reflected by the reflective member 54 through the inspection region R. The return light L6b is fed back to the first light-emitting surface 20a through the inspection region R as the laser beam L4b. When the laser beam L4b is fed back to the first light-emitting surface 20a, a laser beam. L2 having an intensity corresponding to the intensity of the return light L6b, which is absorbed or scattered by the gas to be analyzed, is emitted from the second light-emitting surface 20b. The laser beam L2 is incident on the light incident surface 30a. The laser beam L2 is incident on the light incident surface 30a of the QCD 30, and a signal is output from the QCD 30 through the upper electrode and the lower electrode.

Here, since the mirror 53 is driven so that the direction of the mirror 53 is changed, the wavelength sweep (scan) of the laser beam L4b, which is fed back to the first light-emitting surface 20a from the mirror 53 through the diffraction grating 52, is performed. Accordingly, the laser beam L6a is output to the reflective member 54 with a wavelength that corresponds to the incident angle of the laser beam L5a on the mirror 53. A reduction occurs in the intensity of the return light L6b at a wavelength where the laser beam L6a and the return light L6b are absorbed or scattered by the gas disposed in the inspection region R, so that a change occurs in the oscillation characteristics of the QCL 20. That is, the intensity of the laser beam L2 emitted from the second light-emitting surface 20b is reduced in comparison with the intensity of the laser beam L2 in a case in which the laser beam L6a and the return light L6b are not absorbed or scattered by the gas disposed in the inspection region R. Accordingly, a difference between a signal output from the QCD 30 and a signal (reference signal), which is obtained in a case in which the laser beam L6a and the return light L6b are not absorbed or scattered by the gas disposed in the inspection region R, is taken in the processing circuit provided on the subsequent stage for the analysis of the gas to be analyzed. In this way, differential optical absorption spectroscopy is performed for the gas to be analyzed through the comparison of the signal output from the QCD 30 with the reference signal. Particularly, according to the fluid analyzer 1D, it is possible to perform the analysis (so-called sensing) of the composition of the gas to be analyzed, which is disposed in the inspection region R, while actively changing the oscillation wavelength in a state in which single-mode oscillation is maintained by changing the incident angle on the mirror 53.

According to the fluid analyzer 1D, as described above, an optical resonator is formed between the second light-emitting surface 20b and the mirror 53. The optical resonator oscillates in a single mode with a wavelength, which corresponds to the incident angle of the laser beam L5a diffracted and reflected by the diffraction grating 52 and incident on the mirror 53, as an oscillation wavelength. Accordingly, it is possible to perform the analysis (so-called sensing) of the composition of the gas to be analyzed, which is disposed in the inspection region R, with high sensitivity and high accuracy while actively changing the oscillation wavelength in a state in which single-mode oscillation is maintained by changing the incident angle on the mirror 53.

Fifth Embodiment

Figure 8:
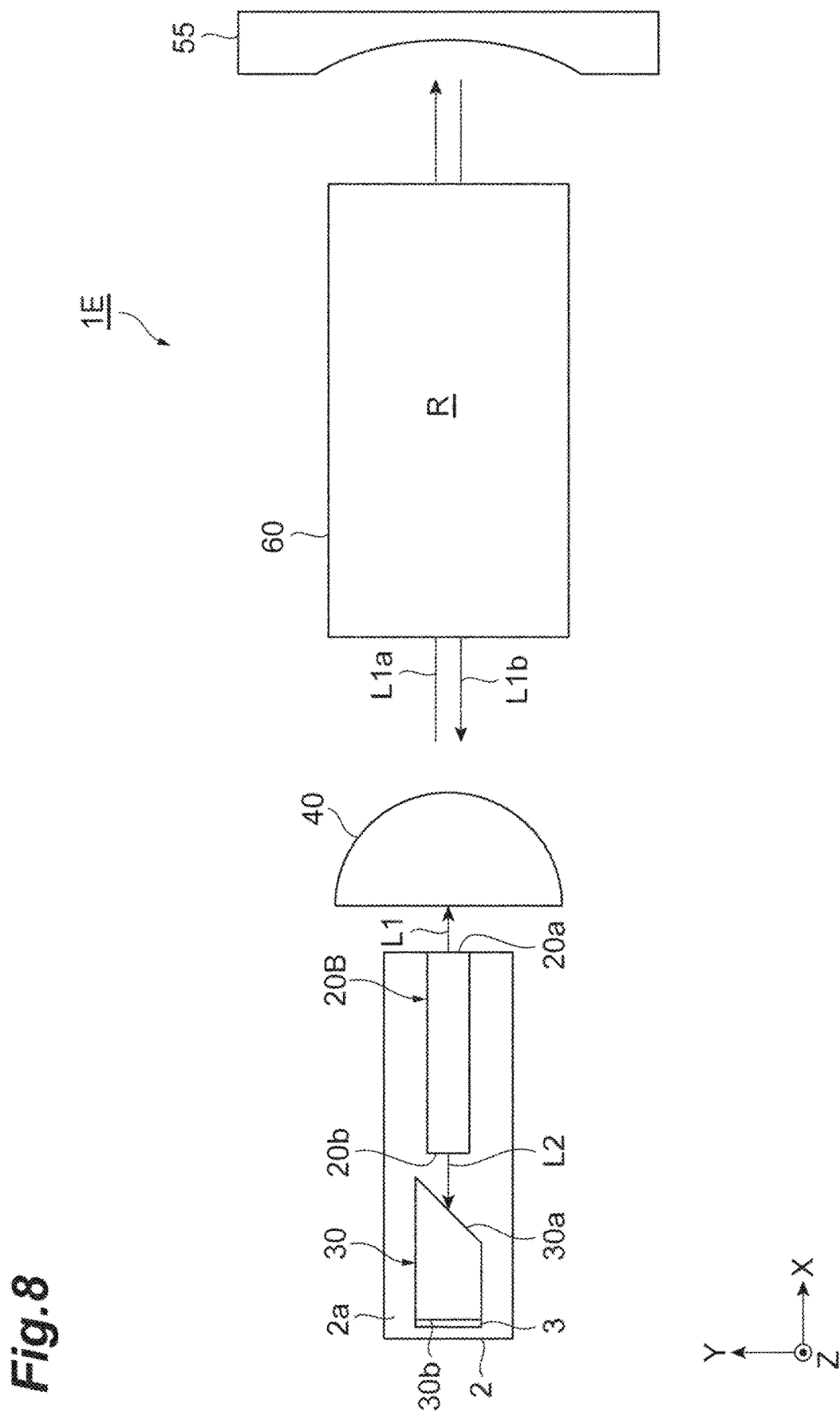
FIG. 8 is a schematic plan view of a fluid analyzer according to a fifth embodiment of the disclosure.

As illustrated in FIG. 8, a fluid analyzer 1E is mainly different from the above-mentioned fluid analyzer 1B in that the fluid analyzer 1E further includes a multi-path cell 60 including an inspection region R therein and includes a concave mirror 55 as the reflective member 50.

The multi-path cell 60 includes, for example, a multireflection mechanism where a plurality of mirrors are used in the inspection region R provided therein. In the multi-path cell 60, for example, the length of a one-way optical path (the length of the optical path of a laser beam L1a or the length of the optical path of return light L1b) may be at least 1 m or more. Accordingly, since the absorption length of light, at which light is absorbed by a gas disposed in the inspection region R, is increased, the analysis of a fluid can be performed with higher sensitivity. Alternatively, the size of the fluid analyzer 1E can be reduced in a state in which the absorption length of light, at which light is absorbed by a gas disposed in the inspection region R, is maintained. Meanwhile, since the length of the optical path is increased by the multi-path cell 60, a QCL 20B oscillating in a single mode may be used in the fluid analyzer 1E.

The concave mirror 55 has, for example, a radius of curvature corresponding to the structure of the multi-path cell 60. The radius of curvature may be a radius of curvature in the range of, for example, 1 to 5 m.

According to the fluid analyzer 1E, as described above, the length of the optical path of the laser beam L1a and the return light L1b in the inspection region R is increased by the multi-path cell 60. For this reason, a change in the intensity of the laser beam L1a and the return light L1b, in a case in which a gas to be analyzed is disposed in the inspection region R, can be made to become more significant.

[Modifications]

The first to fifth embodiments of the disclosure have been described above, but the disclosure is not limited to each of the above-mentioned embodiments. For example, the layer structure 10 of each of the QCL 20, the QCL 20B, and the QCD 30 is not limited to the above-mentioned layer structure. Further, the quantum cascade structure of the active layer 11 of the layer structure 10 is also not limited to the above-mentioned quantum cascade structure.

A fluid to be disposed in the inspection region R is not limited to a gas, and may be a fluid that can absorb or scatter light emitted from the first light-emitting surface 20a.

An example in which the oscillation wavelength of the QCL 20 is set so that the intensity of the laser beam L2 emitted from the second light-emitting surface 20b is reduced due to the absorption of light caused by a gas disposed in the inspection region R has been described in the first embodiment. However, the oscillation wavelength of the QCL 20 may be set so that the intensity of the laser beam L2 emitted from the second light-emitting surface 20b is increased in a case in which a fluid is disposed in the inspection region R. Even in this case, a fluid to be analyzed can be analyzed with high sensitivity and high accuracy since the laser beam L2 emitted from the second light-emitting surface 20b is detected by the QCD 30.

In the first to fifth embodiments, the light incident surface 30a of the QCD 30 is inclined so as to have a positional relationship where an acute angle is formed between the light incident surface 30a and the second light-emitting surface 20b, and is inclined so as to form a right angle together with the X-Y plane perpendicular to the Z-axis direction and so as to form an angle of 45° together with the Y-Z plane perpendicular to the X-axis direction. However, the disclosure is not limited thereto. For example, as illustrated in FIG. 9, a quantum cascade detector 30U (hereinafter, referred to as a "QCD 30U") may be formed on the surface 2a of the substrate 2 instead of the QCD 30.

The structure of the QCD 30U is basically the same as the structure of the QCD 30 except for the structure of a light incident surface 30a. The light incident surface 30a of the QCD 30U is inclined so as to have a positional relationship where an acute angle is formed between the light incident surface 30a and the second light-emitting surface 20b, and is inclined so as to form a right angle together with the Z-X plane perpendicular to the Y-axis direction (an imaginary plane perpendicular to the surface 2a of the substrate 2 and parallel to a predetermined direction) and so as to form an angle θ together with the X-Y plane perpendicular to the Z-axis direction (the surface 2a of the substrate 2). The light incident surface 30a can be formed by, for example, a focused ion beam (FIB) or dry etching that uses a mask of which the thickness is reduced in stages from the QCD 30U toward the QCL 20.

Here, in a case in which the light incident surface 30a is inclined with respect to the second light-emitting surface 20b as described above, it is possible to reduce a reflectance itself on the light incident surface 30a in comparison with a reflectance itself on the light incident surface 30a in a case in which the laser beam L2 is incident on the light incident surface 30a so as to be perpendicular to the light incident surface 30a, in addition to an effect of suppressing the return of the return light of the laser beam L2, which is reflected by the light incident surface 30a, to the second light-emitting surface 20b. Particularly, since the incidence of light on the QCD 30U from the QCL 20 becomes the incidence of light in TM polarization, it is possible to make a reflectance on the light incident surface 30a be infinitely close to zero by setting the angle θ to Brewster's angle.

Figure 9:
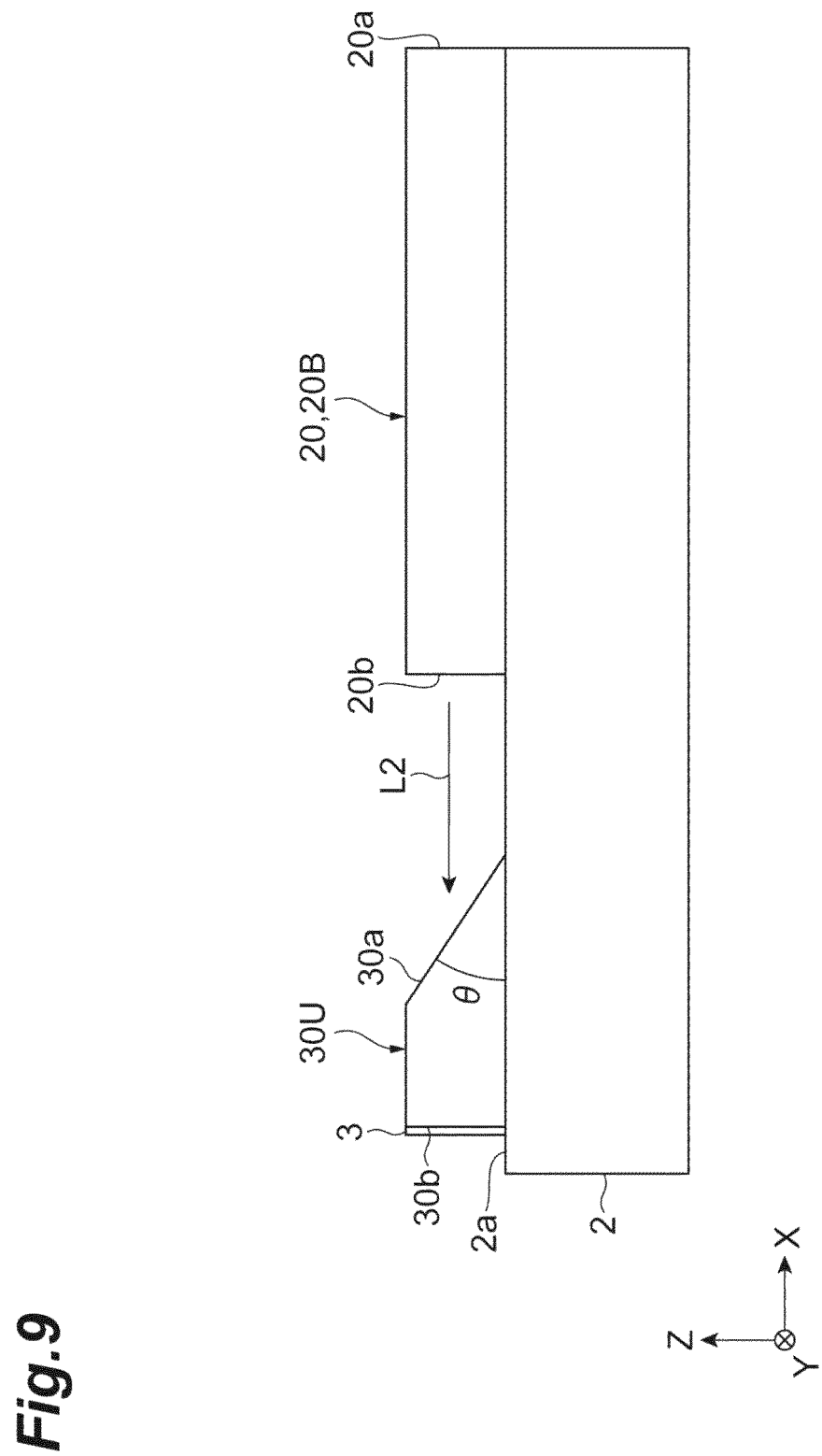
FIG. 9 is a schematic side view of a QCD according to a modification.
Figure 10:
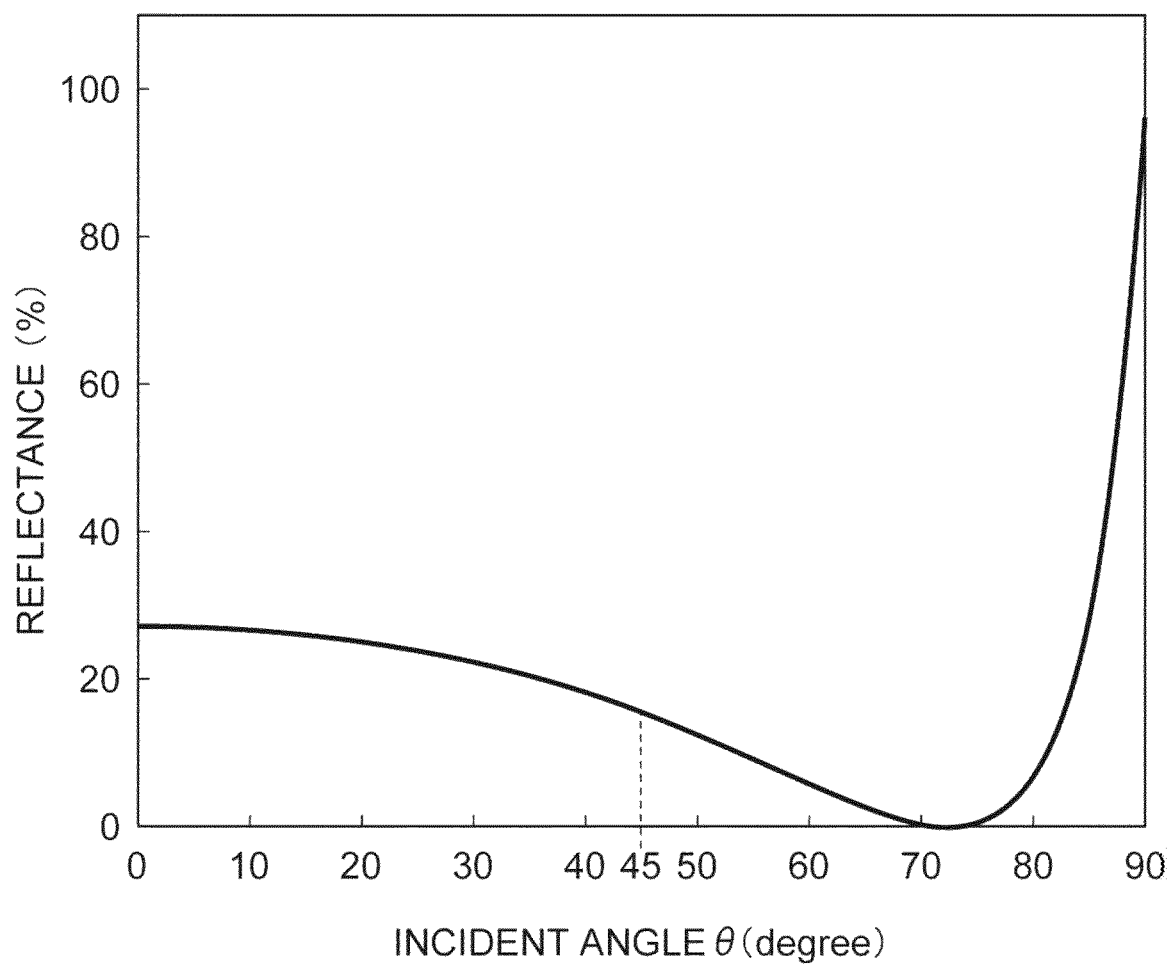
FIG. 10 is a graph illustrating a reflectance on a light incident surface with respect to an angle θ of FIG. 9.

FIG. 10 is a graph illustrating a reflectance on the light incident surface 30a with respect to the angle θ of FIG. 9. A horizontal axis of the graph of FIG. 10 represents the angle θ that is formed between the light incident surface 30a and the surface 2a of the substrate 2, and a vertical axis thereof represents the reflectance of the laser beam L2 on the light incident surface 30a. In the example of FIG. 10, the refractive index of the active layer 11 is set to 3.3 and the refractive index of air is set to 1 to calculate a reflectance. As illustrated in FIG. 10, a reflectance is about 28% or less in a case in which the angle θ is in the range of 0° to 75°. Further, a reflectance is about 17% or less in a case in which the angle θ is in the range of 45° to 75°. Furthermore, a reflectance is about 1% or less in a case in which the angle θ is in the range of 69° to 75°. Moreover, in a case in which the angle θ is about 73° (Brewster's angle), a reflectance is about 0.001% or less and infinitely comes close to zero.

According to the QCD 30U, since it is possible to sufficiently suppress the reflection of the laser beam L2 on the light incident surface 30a, it is possible to efficiently introduce the laser beam L2 into the QCD 30U. Accordingly, it is possible to further suppress an influence of a compound resonator, which is formed between the light incident surface 30a and the first light-emitting surface 20a, on the intensity of the laser beam L2 emitted from the second light-emitting surface 20b. The laser beam L2 can be more reliably absorbed by the QCD 30U.

Figure 11:
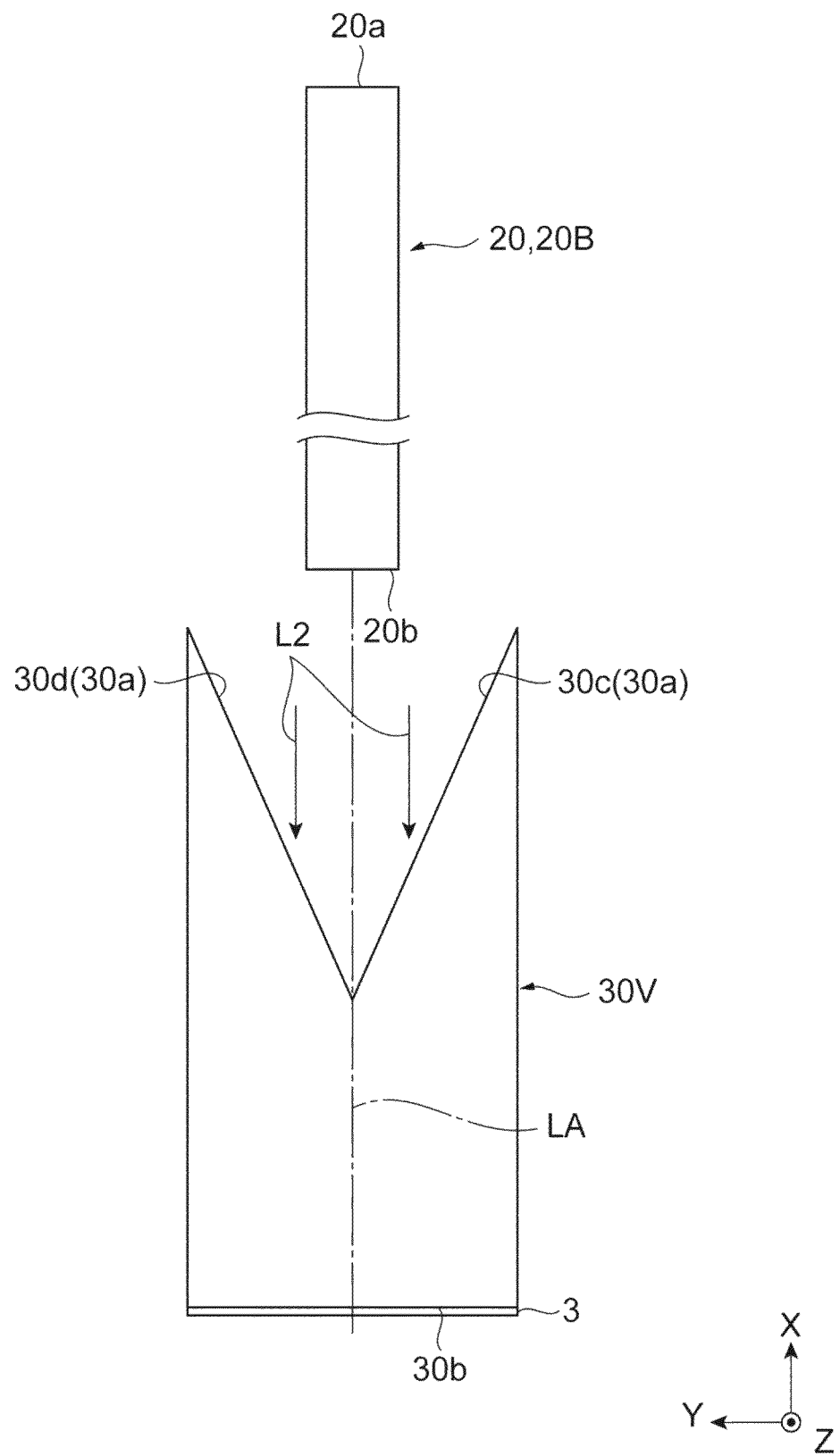
FIG. 11 is a schematic plan view of a QCD according to another modification.

Further, as illustrated in, for example, FIG. 11, a quantum cascade detector 30V (hereinafter, referred to as a "QCD 30V") may be formed on the surface 2a of the substrate 2 instead of the QCD 30.

The structure of the QCD 30V is basically the same as the structure of the QCD 30 except for the shape of a light incident surface 30a. The light incident surface 30a includes a pair of first and second flat surfaces 30c and 30d symmetric with respect to an optical axis LA of the laser beam L2 that is emitted from the second light-emitting surface 20b. The first and second flat surfaces 30c and 30d approach each other as becoming distant from the second light-emitting surface 20b. Accordingly, the first and second flat surfaces 30c and 30d form a V shape in plan view.

According to the QCD 30V, the area of the light incident surface 30a on which the laser beam L2 can be incident can be substantially increased. It is thought that the laser beam L2 is likely to enter the QCD 30V in a case in which the reflection of the laser beam L2 is repeated plural times between the first and second flat surfaces 30c and 30d that form a V shape. According to the QCD 30V, there is a possibility that the QCD 30V can more efficiently receive the laser beam L2 than the QCD 30.

What is claimed is:

1. A fluid analyzer comprising:
   a substrate;
   a quantum cascade laser formed on a surface of the substrate and including a first light-emitting surface and a second light-emitting surface located at opposite ends of the quantum cascade laser in a predetermined direction, the predetermined direction being parallel to the surface of the substrate;
   a quantum cascade detector formed on the surface of the substrate and including a same layer structure as the quantum cascade laser and a light incident surface facing the second light-emitting surface in the predetermined direction; and
   an optical element disposed on an optical path of light emitted from the first light-emitting surface across an inspection region in which a fluid to be analyzed is to be disposed, wherein the optical element is configured to reflect the light to feed a return light to the first light-emitting surface,
   wherein the second light-emitting surface of the quantum cascade laser is configured to transmit an output light to the light incident surface of the quantum cascade detector, and
   wherein an intensity of the output light varies in response to the return light received at the first light-emitting surface of the quantum cascade laser.

2. The fluid analyzer according to claim 1,
   wherein the first light-emitting surface and the second light-emitting surface form an optical resonator to modify the intensity of the output light emitted at the second light-emitting surface, based on an intensity of the return light received at the first light-emitting surface.

3. The fluid analyzer according to claim 2,
   wherein the quantum cascade laser is formed as a Fabry-Perot element oscillating in a multi-mode.

4. The fluid analyzer according to claim 2,
   wherein the quantum cascade laser is formed as a distributed feedback element oscillating in a single mode, and
   a length of the optical path of the light up to the optical element from the first light-emitting surface is an integer multiple of a half of an oscillation wavelength of the quantum cascade laser.

5. The fluid analyzer according to claim 2, wherein the optical resonator is configured to vary in oscillation characteristics, in response to the intensity of the return light received at the first light-emitting surface.

6. The fluid analyzer according to claim 1,
   wherein the optical element is a diffraction grating to diffract and reflect the light emitted from the first light-emitting surface,
   wherein the diffraction grating is configured to reflect, from among the light, light having a wavelength corresponding to an incident angle of the light, and to feed the light having the wavelength back toward the first light-emitting surface, and
   wherein an optical resonator is formed between the second light-emitting surface and the diffraction grating.

7. The fluid analyzer according to claim 1, further comprising:
   a diffraction grating to diffract and reflect the light emitted from the first light-emitting surface; and
   a mirror to reflect the light diffracted and reflected by the diffraction grating,
   wherein the mirror is configured to reflect, from among the light, light having a wavelength corresponding to an incident angle of the light, and to feed the light having the wavelength back toward the first light-emitting surface through the diffraction grating,
   wherein an optical resonator is formed between the second light-emitting surface and the mirror, and wherein the optical element is disposed on an optical path of zero-order reflected light of the light reflected by the diffraction grating across the inspection region in which the fluid to be analyzed is to be disposed, and wherein the optical element is configured to reflect the zero-order reflected light back toward the first light-emitting surface through the diffraction grating.

8. The fluid analyzer according to claim 1, wherein the light incident surface is inclined so as to have a positional relationship where an acute angle is formed between the light incident surface and the second light-emitting surface.

9. The fluid analyzer according to claim 1, wherein the light incident surface is inclined so as to have a positional relationship where an acute angle is formed between the light incident surface and the second light-emitting surface, and is inclined so as to form a right angle together with an imaginary plane perpendicular to the surface of the substrate and parallel to the predetermined direction, and so as to form an angle of 45° or more together with the surface of the substrate.

10. The fluid analyzer according to claim 1, further comprising:
a lens disposed between the first light-emitting surface and the inspection region to collimate the light emitted from the first light-emitting surface.

11. The fluid analyzer according to claim 1, further comprising:
a multi-path cell including the inspection region in the multi-path cell.

12. The fluid analyzer according to claim 1, wherein the quantum cascade detector includes a light reflecting surface facing the light incident surface in the predetermined direction, and
wherein a reflective film configured to reflect the output light emitted from the second light-emitting surface is formed on the light reflecting surface.

13. The fluid analyzer according to claim 1, wherein the first light-emitting surface, the second light-emitting surface, and the optical element form an optical resonator.

14. A fluid analyzer comprising:
a quantum cascade laser having a first light-emitting surface at a first end and a second light-emitting surface located at a second end opposite the first end of the quantum cascade laser, wherein the first light-emitting surface is configured to emit a light along an optical path that intersects an inspection region;
an optical element located along the optical path, to reflect the light that travels from the first light-emitting surface and through the inspection region, and to deliver a return light back to the first light-emitting surface; and
a quantum cascade detector having a light incident surface to receive an output light from the second light-emitting surface, wherein an optical property of the output light is modified in response to the return light received at the first light-emitting surface,
wherein the optical property is an intensity of the output light, and
wherein the first light-emitting surface and the second light-emitting surface form an optical resonator to modify the intensity of the output light emitted at the second light-emitting surface, based on an intensity of the return light received at the first light-emitting surface.

15. The fluid analyzer according to claim 14, wherein the optical resonator is configured to vary in oscillation characteristics, in response to the intensity of the return light received at the first light-emitting surface.

16. The fluid analyzer according to claim 14, wherein the first light-emitting surface, the second light-emitting surface, and the optical element form an optical resonator.

* * * * *